US012617841B2

(12) United States Patent
Weiner et al.

(10) Patent No.: US 12,617,841 B2
(45) Date of Patent: May 5, 2026

(54) NUCLEIC ACID ANTIBODY CONSTRUCTS FOR USE AGAINST RESPIRATORY SYNCYTIAL VIRUS

(71) Applicants: THE WISTAR INSTITUTE OF ANATOMY AND BIOLOGY, Philadelphia, PA (US); INOVIO PHARMACEUTICALS, INC., Plymouth Meeting, PA (US)

(72) Inventors: David Weiner, Merion, PA (US); Kar Muthumani, Cherry Hill, NJ (US); Jing Chen, Merion Station, PA (US); Trevor Smith, San Diego, CA (US); Katherine Schultheis, San Diego, CA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 1138 days.

(21) Appl. No.: 16/966,506

(22) PCT Filed: Jan. 31, 2019

(86) PCT No.: PCT/US2019/015975
§ 371 (c)(1),
(2) Date: Jul. 31, 2020

(87) PCT Pub. No.: WO2019/152600
PCT Pub. Date: Aug. 8, 2019

(65) Prior Publication Data
US 2021/0047390 A1      Feb. 18, 2021

Related U.S. Application Data

(60) Provisional application No. 62/749,580, filed on Oct. 23, 2018, provisional application No. 62/624,320, filed on Jan. 31, 2018.

(51) Int. Cl.
| | |
|---|---|
| C07K 16/10 | (2006.01) |
| A61K 39/42 | (2006.01) |
| A61K 48/00 | (2006.01) |
| A61P 11/00 | (2006.01) |
| A61P 31/14 | (2006.01) |

(52) U.S. Cl.
CPC .......... C07K 16/1027 (2013.01); A61K 39/42 (2013.01); A61K 48/005 (2013.01); A61P 11/00 (2018.01); A61P 31/14 (2018.01); C07K 2317/76 (2013.01)

(58) Field of Classification Search
CPC .............. A61P 31/14; A61K 2039/505; A61K 2039/53; A61K 31/7088; C12N 15/11; C12N 15/62; C07K 16/1027
See application file for complete search history.

(56) References Cited

U.S. PATENT DOCUMENTS

| | | | | |
|---|---|---|---|---|
| 9,221,917 | B2 | 12/2015 | Baurin | |
| 2004/0005324 | A1* | 1/2004 | Pilkington | ......... C07K 16/1027 530/388.3 |
| 2011/0066111 | A1 | 3/2011 | Teschner | |
| 2012/0070446 | A1* | 3/2012 | Beaumont | .......... A61K 31/7088 435/339 |
| 2013/0177573 | A1* | 7/2013 | Williamson | ........... A61K 45/06 435/5 |
| 2014/0271653 | A1* | 9/2014 | Gurnett-Bander | ...... A61P 11/00 435/339 |
| 2015/0284448 | A1 | 10/2015 | Weiner | |
| 2016/0311891 | A1* | 10/2016 | Weiner | .................. C07K 16/10 |
| 2016/0340414 | A1* | 11/2016 | Ulbrandt | ............ C07K 16/1027 |
| 2016/0340427 | A1 | 11/2016 | Chang | |
| 2017/0121394 | A1* | 5/2017 | Vora | ........................ A61P 43/00 |

FOREIGN PATENT DOCUMENTS

| | | |
|---|---|---|
| WO | 2000053623 | 9/2000 |
| WO | 2004083373 | 9/2004 |
| WO | 2010095031 | 8/2010 |
| WO | 2012135345 | 10/2012 |
| WO | 2012145572 | 10/2012 |
| WO | 2015089492 | 6/2015 |
| WO | 2016145385 | 9/2016 |
| WO | 2016184426 | 11/2016 |
| WO | 2017040529 | 3/2017 |
| WO | 2017193094 | 11/2017 |
| WO | 2017193101 | 11/2017 |

OTHER PUBLICATIONS

Tycko et al., Intranasal delivery of neutralizing antibodies by AAV9 to protect mice against RSV infection, Molecular Therapy, vol. 22, supplement 1, p. S271, abstract No. 701. (Year: 2014).*
Antepowicz et al., Delivery of therapeutic monoclonal antibody genes for prophylaxis of respiratory syncytial virus infection, Molecular Therapy, vol. 25, No. 5, supplement 1, pp. 94-95, abstract No. 199. (Year: 2017).*
Schultheis et al., Functional characterization of in vivo expressed DNA-based monoclonal antibodies (dMAbs) against repiratory syncytial virus (RSV), Molecular Therapy, vol. 26, No. 5S1, p. 244, abstract No. 523. (Year: 2018).*
Hu et al., Codon optimization, expression, and characterization of an internalizing anti-ErbB2 single-chain antibody in Pichia pastoris, Protein Expression & Purification, vol. 47, pp. 249-257. (Year: 2006).*

(Continued)

*Primary Examiner* — Dana H Shin
(74) *Attorney, Agent, or Firm* — Riverside Law LLP

(57) ABSTRACT

Disclosed herein is a composition including a recombinant nucleic acid sequence that encodes an antibody to a Respiratory Syncytial Virus antigen. Also disclosed herein is a method of generating a synthetic antibody in a subject by administering the composition to the subject. The disclosure also provides a method of preventing and/or treating an Respiratory Syncytial virus infection in a subject using the composition and method of generation.

8 Claims, 18 Drawing Sheets

Specification includes a Sequence Listing.

(56) References Cited

OTHER PUBLICATIONS

Ternette et al., Immunogenicity and efficacy of codon optimized DNA vaccines encoding the F-protein of respiratory syncytial virus, Vaccine, vol. 25, pp. 7271-7279. (Year: 2007).*

Audet et al: Molecular Characterization of the Monoclonal Antibodies Composing ZMAb: A Protective Cocktail Against Ebola Virus| , Scientific Reports, vol. 4, No. 1, Nov. 6, 2014 (Nov. 6, 2014).

Bishnu et al: "Rapid/sustained anti-anthrax passive immunity mediated by co• administration of Ad/AAV", Molecular Therapy, vol. 16, No. 1, Jan. 1, 2008, pp. 203-209.

Bornholdt et al: "Isolation of potent neutralizing antibodies from a survivor of the 2014 Ebola virus outbreak (Author Manuscript)", Science, vol. 351, No. 6277, Feb. 18, 2016 (Feb. 18, 2016), pp. 1078-1083.

Limberis et al: "Adena-Associated Virus Serotype 9-Expressed ZMapp in Mice Confers Protection Against Systemic and Airway-Acquired Ebola Virus Infection", Journal of Infectious Diseases, vol. 214, No. 12, Sep. 28, 2016, pp. 1975-1979.

Smith et al, "Nucleic acid-based vaccines targeting respiratory syncytial virus: Delivering the goods", Human Vaccines & Immunotherapeutics, US, vol. 13, No. 11, (Nov. 2, 2017), pp. 2626-2629.

Wec et al, "Antibodies from a Human Survivor Define Sites of Vulnerability for Broad Protection against Ebolaviruses", Cell, Amsterdam NL, (May 1, 2017), vol. 169, No. 5, pp. 878-890.e15.

* cited by examiner

1B

1D

1A

1C

1: No Treatment
2: pVax
3: dMAb (perpendicular)
4: dMAb (parallel)

5A

NUCLEIC ACID ANTIBODY CONSTRUCTS FOR USE AGAINST RESPIRATORY SYNCYTIAL VIRUS

TECHNICAL FIELD

The present invention relates to a composition comprising a recombinant nucleic acid sequence for generating one or more synthetic antibodies, and functional fragments thereof, in vivo, and a method of preventing and/or treating viral infection in a subject by administering said composition.

CROSS-REFERENCE TO RELATED APPLICATIONS

This application is a U.S. national phase application filed under 35 U.S.C. § 371 claiming priority to International Patent Application No. PCT/US19/15975, filed Jan. 31, 2019, which is entitled to priority under 35 U.S.C. § 119(e) to U.S. Provisional Application No. 62/624,320, filed Jan. 31, 2018, and U.S. Provisional Application No. 62/749,580, filed Oct. 23, 2018, the contents of each of which are incorporated by reference herein in their entireties.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206193-0111-00US_Sequence_Listing_v2.txt" in ASCII format. The text file containing the Sequence Listing of the present application was created on Sep. 25, 2024, and is 39,491 bytes in size.

BACKGROUND

Respiratory Syncytial virus (RSV) is a major threat to the health of young children and elderly adults, and complications involved with lower respiratory infections can lead to hospitalization and, some patients may succumb to disease. Almost the entire population is infected with the virus during the first years of life, but immunity in many cases is not sustained nor completely protective against following infections. Even though a vaccine remains an unmet need, passive immunization with an immunoprophylactic anti-RSV-F antibody (Pavilizumab) has successfully reduced hospitalizations in vulnerable patients. However, the use of this monoclonal Antibody (mAb) is limited to high resource settings and unavailable to the majority of the global at risk populations.

While mAbs have been shown to be effective in providing protection against many infectious diseases their widespread use is limited. The limited in vivo half-life means multiple doses are required to maintain immunity, and the high costs and complexities involved in development, manufacture and distribution also hinder their global use. In response, new strategies based on the in vivo delivery of antibody genes are being developed. One such platform is dMAb, a synthetic DNA-encoded mAb delivered by electrogenetransfer in vivo and utilizing the body's own muscle cells to generate and secrete the protein immunoglobulin. Other than protein-based drugs, plasmid DNA is inexpensive to manufacture and because of its temperature stability it would not require a cold chain, which makes it ideal for global distribution. In proof-of principle studies this platform provided protection against various infectious diseases, including influenza, pseudomonas and Ebola in pre-clinical animal models.

Thus, there is need in the art for improved therapeutics that prevent and/or treat RSV infection. The current invention satisfies this need.

SUMMARY

The present invention is directed to a nucleic acid molecule encoding one or more synthetic antibodies, wherein the nucleic acid molecule comprises at least one selected from the group consisting of a) a nucleotide sequence encoding an anti-respiratory syncytial virus (RSV) synthetic antibody; b) a nucleotide sequence encoding a fragment of an anti-RSV synthetic antibody; c) a nucleotide sequence encoding ScFv anti-RSV synthetic antibody; and d) a nucleotide sequence encoding a fragment of a ScFv anti-RSV synthetic antibody. In one embodiment, the invention relates to a nucleic acid molecule encoding a ScFv anti-RSV DMAb or a fragment or variant thereof. In one embodiment, the invention relates to a nucleic acid molecule encoding an anti-RSV antibody or a fragment or variant thereof.

In one embodiment, the synthetic antibody binds to an RSV antigen. In one embodiment, the synthetic antibody binds to one or more RSV antigens selected from RSV-F, RSV-G, RSV-Ga, RSV-Gb, RSV-M2-1, RSV M2-2, and any combination thereof.

In one embodiment, the nucleic acid molecule comprises nucleotide sequence encoding a cleavage domain.

In one embodiment, the nucleic acid molecule comprises a nucleotide sequence encoding an amino acid sequence at least 90% homologous to an amino acid sequence selected from the group consisting of: SEQ ID NO:7 and an amino acid sequence encoded by one of SEQ ID NOs: 1-6; or a fragment of an amino acid sequence at least 90% homologous to an amino acid sequence selected from the group consisting of SEQ ID NO:7 and an amino acid sequence encoded by one of SEQ ID NOs: 1-6. In one embodiment, the nucleic acid molecule comprises a nucleotide sequence at least 90% homologous to SEQ ID NOs: 1-6 or a fragment of a nucleotide sequence at least 90% homologous to SEQ ID NOs: 1-6.

In one embodiment, the nucleotide sequence encodes a leader sequence.

In one embodiment, the nucleic acid molecule comprises an expression vector.

In one embodiment, the invention provides a composition comprising a nucleic acid molecule of the invention. In one embodiment, the composition comprises a pharmaceutically acceptable excipient. In one embodiment, the composition comprises hyaluronidase.

In one embodiment, the invention provides an anti-RSV monoclonal antibody. In one embodiment, the anti-RSV monoclonal antibody comprises an amino acid sequence that is at least 90% homologous to the amino acid sequence selected from the group consisting of SEQ ID NO:7 and an amino acid sequence encoded by one of SEQ ID NOs: 1-6; or a fragment of an amino acid sequence at least 90% homologous to the amino acid sequence selected from the group consisting of SEQ ID NO:7 and an amino acid sequence encoded by one of SEQ ID NOs: 1-6.

In one embodiment, the invention provides a formulation comprising a nucleic acid molecule of the invention. In one embodiment, the formulation comprises hyaluronidase.

In one embodiment, the invention provides a method of preventing or treating a disease in a subject. In one embodiment, the method comprises administering a nucleic acid molecule, composition, formulation or anti-RSV monoclonal antibody to the subject. In one embodiment, the disease is a Respiratory Syncytial virus infection.

BRIEF DESCRIPTION OF THE DRAWINGS

FIG. 1A depicts an illustration of human IgG1 and scFv-Fc formats. The complete hinge and Fc portions of the molecule are retained in the scFv-Fc format. FIG. 1B depicts a plasmid map of RSV-F dMAb. FIG. 1C depicts in vitro expression of RSV-F dMAb. Immuno-fluorescence staining was performed on 293 T cells 3 days after transfection (DAPI, RSV-F dMAb). FIG. 1C depicts western-blot analysis of cell-culture supernatant of RSV-F dMAb in-vitro transfected HEK293T cells harvested after 3 days (lane 1: IgG-RSV dMAb, lane 2: sc-Fv-Fc RSV-F dMAb).

FIG. 2A through FIG. 2C, depicts the RSV-F dMAb in-vivo delivery platform. FIG. 2A depicts in vivo electroporation facilitates the delivery of the dMAb to the muscle tissue, myocytes express and secret the encoded MAb. MAb is distributed systemically. FIG. 2B depicts an example of expression of dMAb in myocytes after dMAb delivery to mouse TA muscle (DAPI, dMAb). FIG. 2C depicts serum concentration of human IgG after dMAb delivery measured by ELISA (+/−SEM, n=7).

FIG. 3A depicts serum expression of RSV-F dmAb. Sc-Fv-Fc construct (+/−SEM, n=5-8) FIG. 3B depicts RSV-F antigen binding of dMAb. RSV-F binding signal of serum samples (+/−SEM, n=4) FIG. 3C depicts neutralization of RSV-A virus. Neutralization titer (log 2 serum dilution of 60% reduction of plaque-formation; +/−SEM, n=3-11, dotted line indicates LOD at serum-dilution of 1/20) FIG. 3D depicts the concentration of sc-Fv-Fc RSV-F dMAb in BAL samples 7 days after RSV-dMAb pDNA delivery (mol sc-Fv-Fc dMAb per gram total protein in lavage sample).

FIG. 4A depicts local expression of dMAb demonstrated by Immunofluorescence staining of RSV-F dMAb in cotton rat TA muscle tissue 7 days after delivery of RSV-F dMAb pDNA to the tissue site (DAPI; RSV-F dMAb; sectioned perpendicular to myocytes). FIG. 4B depicts the levels of RSV-F dMAb (ng/ml) was measured for 39 days after IM administration of 800 μg dMAb-plasmid (+/−SEM, n=5).

FIG. 4C depicts virus neutralization function of in-vivo expressed RSV-F dMAb. Serum samples were harvested and tested 7 days after delivery of 2.4 mg sc-Fv-Fc dMAb-pDNA: neutralizing titer (+/−SEM, dotted line indicates LOD at serum-dilution of 1/20). FIG. 4D depicts the concentration of RSV-F dMAb in BAL samples from treated cotton rats.

FIG. 5A through FIG. 5D, depicts experimental results demonstrating that RSV-F dMAb confers protection against Lower Respiratory Disease in live virus challenge of cotton rats. FIG. 5A depicts a schematic of cotton rat challenge study: Animals were treated with 2.4 mg RSV-dMAb 7 days before challenge, IM injection of 15 mg/kg Palivizumab 1 day before challenge. FIG. 5B depicts the viral load of cotton rat lung tissue (pfu/g) harvested 5 days after intra-nasal live virus challenge with RSV/A/long (+/−SEM n=4-5). FIG. 5C depicts RSV mRNA levels (log 2 and normalized to beta-Actin) of cotton rat lung tissue 5 days after intra-nasal live virus challenge with RSV/A/long (+/−SEM, n=4-5, Mann-Whitney non-parametric t-test: p (untreated vs RSV-dMAb)=0.0159; p (untreated vs Palivizumab)=0.0079). FIG. 5D depicts serum levels of Palivizumab and sc-Fv-Fc RSV-F dMAb in cotton rats at day of challenge (day 7) and 5 days after challenge (+/−SEM, n=4-5).

DETAILED DESCRIPTION

Figure 1:
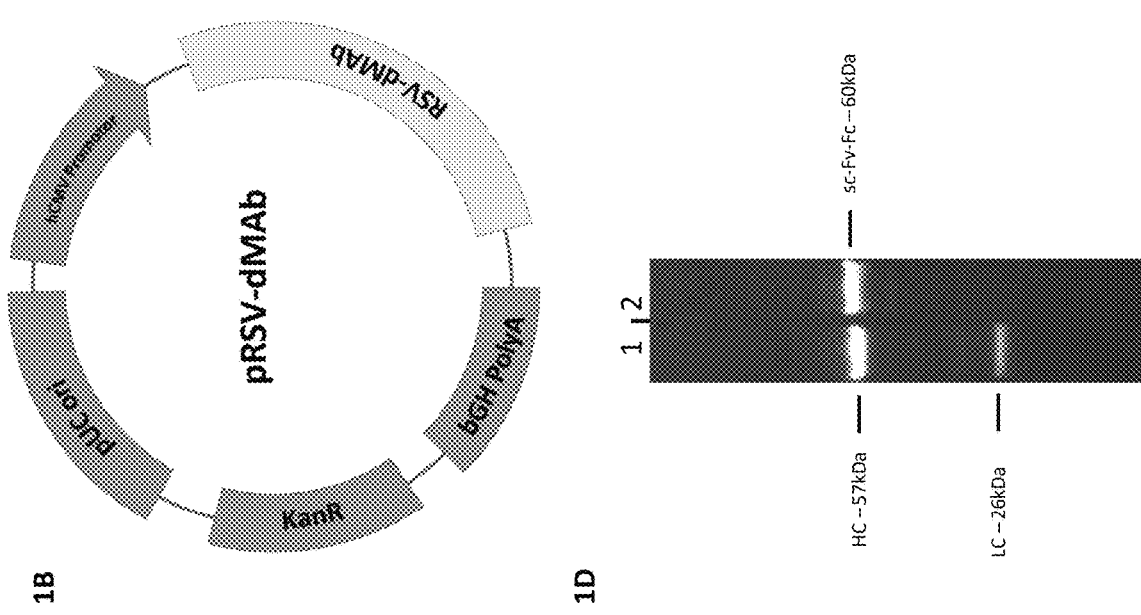
FIG. 1, comprising FIG. 1A through FIG. 1D depicts the design and in-vitro testing of sc-Fv-Fc RSV-FdMAb construct.
Figure 1:
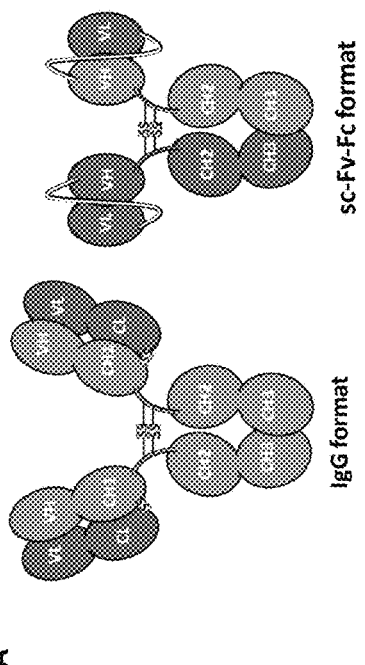
Figure 1:
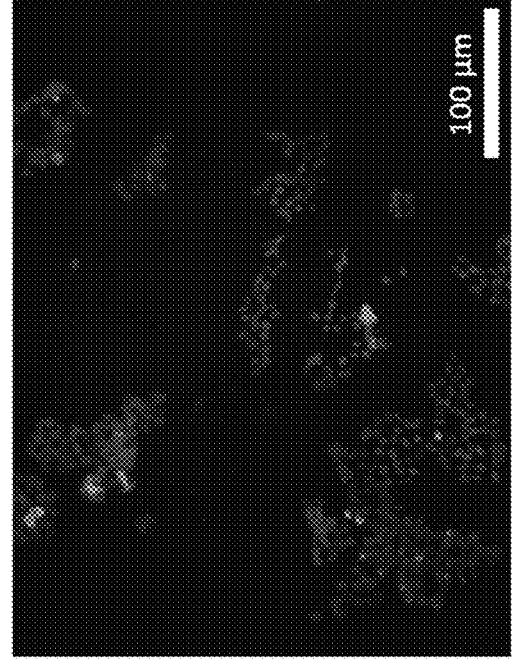

The present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody.

In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the antigen, being more immunogenic as compared to an antibody not assembled as described herein, and being capable of eliciting or inducing an immune response against the antigen.

Additionally, these synthetic antibodies are generated more rapidly in the subject than antibodies that are produced in response to antigen induced immune response. The synthetic antibodies are able to effectively bind and neutralize a range of antigens. The synthetic antibodies are also able to effectively protect against and/or promote survival of disease.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise.

The present disclosure also contemplates other embodiments, "comprising," "consisting of" and "consisting essentially of," the embodiments, or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

"Coding sequence" or "encoding nucleic acid" as used herein may mean refers to the nucleic acid (RNA or DNA molecule) that comprise a nucleotide sequence which encodes an antibody as set forth herein. The coding sequence may also comprise a DNA sequence which encodes an RNA sequence. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full-length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide.

The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The genetic construct may also refer to a DNA molecule which transcribes an RNA. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of 2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within +2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOSITION

The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody in the subject. The synthetic antibody can bind a target molecule (i.e., an antigen) present in the subject. Such binding can neutralize the antigen, block recognition of the antigen by another molecule, for example, a protein or nucleic acid, and elicit or induce an immune response to the antigen.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In one embodiment, the nucleic acid molecule comprises a nucleotide sequence encoding an anti-Respiratory syncytial virus (anti-RSV) antibody.

In one embodiment, the nucleotide sequence encoding an anti-RSV antibody comprises one or more codon optimized nucleic acid sequences encoding an amino acid sequence that is at least 90% homologous to the amino acid sequence encoded by one of SEQ ID NOs: 1-6, or a fragment of an amino acid sequence that is at least 90% homologous to the amino acid sequence encoded by one of SEQ ID NOs: 1-6. In one embodiment, the nucleotide sequence encoding an anti-RSV antibody comprises one or more codon optimized nucleic acid sequences encoding an amino acid sequence that is at least 90% homologous to SEQ ID NO:7, or a fragment of an amino acid sequence that is at least 90% homologous to SEQ ID NO:7. In one embodiment, the nucleotide sequence encoding an anti-RSV antibody comprises one or more nucleic acid sequences encoding the amino acid sequence encoded by One of SEQ ID NOs: 1-6, or a fragment of the amino acid sequence encoded by one of SEQ ID NOs: 1-6. In one embodiment, the nucleotide sequence encoding an anti-RSV antibody comprises one or more nucleic acid sequences encoding SEQ ID NO:7, or a fragment SEQ ID NO:7.

In one embodiment, the nucleotide sequence encoding an anti-RSV antibody comprises one or more RNA sequence transcribed from one or more DNA sequences encoding an amino acid sequence that is at least 90% homologous to the amino acid sequence encoded by one of SEQ ID NOs: 1-6 or a fragment of an amino acid sequence at least 90% homologous to the amino acid sequence encoded by one of SEQ ID NOs: 1-6. In one embodiment, the nucleotide sequence encoding an anti-RSV antibody comprises one or more RNA sequence transcribed from one or more DNA sequences encoding an amino acid sequence that is at least 90% homologous to SEQ ID NO:7 or a fragment of SEQ ID NO:7. In one embodiment, the nucleotide sequence encoding an anti-RSV antibody comprises one or more RNA sequence transcribed from one or more DNA sequences encoding the amino acid sequence encoded by One of SEQ ID NOs: 1-6 or a fragment of the amino acid sequence encoded by one of SEQ ID NOs: 1-6. In one embodiment, the nucleotide sequence encoding an anti-RSV antibody comprises one or more RNA sequence transcribed from one or more DNA sequences encoding an amino acid sequence of SEQ ID NO:7 or a fragment of SEQ ID NO:7.

In one embodiment, the nucleotide sequence encoding an anti-RSV antibody comprises one or more codon optimized nucleic acid sequences at least 90% homologous to SEQ ID NO: 1-6 or a fragment of a nucleic acid sequence at least 90% homologous to SEQ ID NO: 1-6. In one embodiment, the nucleotide sequence encoding an anti-RSV antibody comprises one or more codon optimized nucleic acid sequences as set forth in SEQ ID NO: 1-6 or a fragment of a nucleic acid sequence as set forth in SEQ ID NO: 1-6.

In one embodiment, the nucleotide sequence encoding an anti-RSV antibody comprises one or more RNA sequence transcribed from one or more DNA sequences at least 90% homologous to SEQ ID NO: 1-6 or a fragment of a DNA sequence at least 90% homologous to SEQ ID NO: 1-6. In one embodiment, the nucleotide sequence encoding an anti-RSV antibody comprises one or more RNA sequence transcribed from one or more DNA sequences as set forth in SEQ ID NO: 1-6 or a fragment of a DNA sequence as set forth in SEQ ID NO: 1-6.

In one embodiment, the composition comprises a nucleotide sequence encoding a synthetic RSV heavy chain. In one embodiment, the composition comprises a nucleotide sequence encoding a synthetic RSV light chain. In one embodiment, the composition comprises a nucleotide sequence encoding a synthetic RSV antibody. In one embodiment, the sequence encoding a synthetic RSV antibody comprises a first sequence encoding a synthetic RSV heavy chain and a second sequence encoding a synthetic RSV light chain.

The composition of the invention can treat, prevent and/or protect against any disease, disorder, or condition associated with Respiratory Syncytial virus infection. In certain embodiments, the composition can treat, prevent, and or/protect against viral infection. In certain embodiments, the composition can treat, prevent, and or/protect against condition associated with Respiratory Syncytial virus infection.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the synthetic antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability and low cost per dose.

3. RECOMBINANT NUCLEIC ACID SEQUENCE

As described above, the composition can comprise a recombinant nucleic acid sequence. The recombinant nucleic acid sequence can encode the antibody, a fragment thereof, a variant thereof, or a combination thereof. The antibody is described in more detail below.

The recombinant nucleic acid sequence can be a heterologous nucleic acid sequence. The recombinant nucleic acid sequence can include one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; addition of an internal IRES sequence and eliminating to the extent possible cis-acting sequence motifs (i.e., internal TATA boxes).

Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can also include a heterologous nucleic acid sequence that encodes an internal ribosome entry site (IRES). An IRES may be either a viral IRES or a eukaryotic IRES. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDRT," "CDR2," and "CDR3," respectively. CDR1, CDR2, and CDR3 of the heavy chain polypeptide can contribute to binding or recognition of the antigen.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDRT," "CDR2," and "CDR3," respectively. CDR1, CDR2, and CDR3 of the light chain polypeptide can contribute to binding or recognition of the antigen.

(3) Protease Cleavage Site

The recombinant nucleic acid sequence construct can include heterologous nucleic acid sequence encoding a protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human 3-globin polyadenylation signal. The SV40 polyadenylation signal may be a polyadenylation signal from a pCEP4 plasmid (Invitrogen, San Diego, CA).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(12) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide. For example, in one embodiment, the first recombinant nucleic acid sequence encodes a heavy chain polypeptide. In one embodiment, the second recombinant nucleic acid sequence encodes a light chain polypeptide.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(13) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A forth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

(14) ScFv Arrangement

In a ScFv arrangement, the recombinant nucleic acid sequence can include a sequence encoding the VH domain of the heavy chain polypeptide, and the VL domain of the light chain polypeptide, and optionally further a linker sequence positioned between the heterologous nucleic acid sequence encoding the VH domain and VL domain.

An example of a ScFv arrangement can include the vector (and thus recombinant nucleic acid sequence construct) encoding the VH, linker, VL, hinge region, CH2, and CH3. The VH region can be N-terminally or C-terminally linked to a VL region via a linker.

Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

Vector

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. In some embodiments, the vector includes linear DNA, enzymatic DNA or synthetic DNA. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(15) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(16) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif), which may be used for protein production in mammalian cells such as Chinese hamster ovary (CHO) cells.

(17) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID NO: 1-6 or a fragment of a DNA sequence at least 90% homologous to one of SEQ ID NO: 1-6. In another embodiment, the nucleotide sequence comprises an RNA sequence transcribed by a DNA sequence encoding a polypeptide sequence at least 90% homologous to one of the amino acid sequence encoded by one of SEQ ID NOs: 1-6, a fragment of an amino acid sequence at least 90% homologous to the amino acid sequence encoded by one of SEQ ID NOs: 1-6, or a variant thereof or a fragment thereof. In one embodiment, the nucleotide sequence comprises an RNA sequence transcribed by a DNA sequence encoding a polypeptide sequence at least 90% homologous SEQ ID NO:7, a fragment of an amino acid sequence at least 90% homologous SEQ ID NO:7, or a variant thereof or a fragment thereof. Accordingly, in one embodiment, the invention provides an RNA molecule encoding one or more of the MAbs or DMAbs. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

(18) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or μM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be pcrM2. The LEC can be pcrNP. pcrNP and pcrMR can be derived from pNP (Puerto Rico/34) and μM2 (New Caledonia/99), respectively.

(19) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585, 362.

(20) Method of Preparing the Vector

Provided herein is a method for preparing the one or more vectors in which the recombinant nucleic acid sequence construct has been placed. After the final subcloning step, the vector can be used to inoculate a cell culture in a large-scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939, 792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

4. ANTIBODY

As described above, the recombinant nucleic acid sequence can encode the antibody, a fragment thereof, a variant thereof, or a combination thereof. The antibody can bind or react with the antigen, which is described in more detail below.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab')$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject. Such modifications are described below in more detail.

The antibody can be defucosylated as described in more detail below.

The antibody may be modified to reduce or prevent antibody-dependent enhancement (ADE) of disease associated with the antigen as described in more detail below.

ScFv Antibody

In one embodiment, the DMAb of the invention is a ScFv DMAb. In one embodiment, ScFv DMAb relates to a Fab fragment without the of CH1 and CL regions. Thus, in one embodiment, the ScFv DMAb relates to a Fab fragment DMAb comprising the VH and VL. In one embodiment, the ScFv DMAb comprises a linker between VH and VL. In one embodiment, the ScFv DMAb is an ScFv-Fc DMAb. In one embodiment, the ScFv-Fc DMAb comprises the VH, VL and the CH2 and CH3 regions. In one embodiment, the ScFv-Fc DMAb comprises a linker between VH and VL. In one embodiment, the ScFv DMAb of the invention has modified expression, stability, half-life, antigen binding, heavy chain—light chain pairing, tissue penetration or a combination thereof as compared to a parental DMAb.

In one embodiment, the ScFv DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher expression than the parental DMAb.

In one embodiment, the ScFv DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher antigen binding than the parental DMAb.

In one embodiment, the ScFv DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold longer half-life than the parental DMAb.

In one embodiment, the ScFv DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher stability than the parental DMAb.

In one embodiment, the ScFv DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold greater tissue penetration than the parental DMAb.

In one embodiment, the ScFv DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold greater heavy chain—light chain pairing than the parental DMAb.

Bispecific Antibody

The recombinant nucleic acid sequence can encode a bispecific antibody, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker.

The invention provides novel bispecific antibodies comprising a first antigen-binding site that specifically binds to a first target and a second antigen-binding site that specifically binds to a second target, with particularly advantageous properties such as producibility, stability, binding affinity, biological activity, specific targeting of certain T cells, targeting efficiency and reduced toxicity. In some instances, there are bispecific antibodies, wherein the bispecific antibody binds to the first target with high affinity and to the second target with low affinity. In other instances, there are bispecific antibodies, wherein the bispecific antibody binds to the first target with low affinity and to the second target with high affinity. In other instances, there are bispecific antibodies, wherein the bispecific antibody binds to the first target with a desired affinity and to the second target with a desired affinity.

In one embodiment, the bispecific antibody is a bivalent antibody comprising a) a first light chain and a first heavy chain of an antibody specifically binding to a first antigen, and b) a second light chain and a second heavy chain of an antibody specifically binding to a second antigen.

A bispecific antibody molecule according to the invention may have two binding sites of any desired specificity. In some embodiments, one of the binding sites is capable of an RSV antigen. In some embodiments, the binding site included in the Fab fragment is a binding site specific for a RSV antigen. In some embodiments, the binding site included in the single chain Fv fragment is a binding site specific for a RSV antigen such as a RSV capsid antigen or a RSV envelope antigen, for example RSV-F, RSV-G, RSV-Ga, RSV-Gb, RSV-M2-1, or RSV M2-2.

In some embodiments, one of the binding sites of an antibody molecule according to the invention is able to bind a T-cell specific receptor molecule and/or a natural killer cell (NK cell) specific receptor molecule. A T-cell specific receptor is the so called "T-cell receptor" (TCRs), which allows a T cell to bind to and, if additional signals are present, to be activated by and respond to an epitope/antigen presented by another cell called the antigen-presenting cell or APC. The T cell receptor is known to resemble a Fab fragment of a naturally occurring immunoglobulin. It is generally mon-ovalent, encompassing .alpha.- and .beta.-chains, in some embodiments, it encompasses .gamma.-chains and .delta.-chains (supra). Accordingly, in some embodiments, the TCR is TCR (alpha/beta) and in some embodiments, it is TCR (gamma/delta). The T cell receptor forms a complex with the CD3 T-Cell co-receptor. CD3 is a protein complex and is composed of four distinct chains. In mammals, the complex contains a CD3γ chain, a CD36 chain, and two CD3E chains. These chains associate with a molecule known as the T cell receptor (TCR) and the ξ-chain to generate an activation signal in T lymphocytes. Hence, in some embodiments, a T-cell specific receptor is the CD3 T-Cell co-receptor. In some embodiments, a T-cell specific receptor is CD28, a protein that is also expressed on T cells. CD28 can provide co-stimulatory signals, which are required for T cell activa-tion. CD28 plays important roles in T-cell proliferation and survival, cytokine production, and T-helper type-2 develop-ment. Yet a further example of a T-cell specific receptor is CD134, also termed Ox40. CD134/OX40 is being expressed after 24 to 72 hours following activation and can be taken to define a secondary costimulatory molecule. Another example of a T-cell receptor is 4-1 BB capable of binding to 4-1 BB-Ligand on antigen presenting cells (APCs), whereby a costimulatory signal for the T cell is generated. Another example of a receptor predominantly found on T-cells is CD5, which is also found on B cells at low levels. A further example of a receptor modifying T cell functions is CD95, also known as the Fas receptor, which mediates apoptotic signaling by Fas-ligand expressed on the surface of other cells. CD95 has been reported to modulate TCR/CD3-driven signaling pathways in resting T lymphocytes.

An example of a NK cell specific receptor molecule is CD16, a low affinity Fc receptor and NKG2D. An example of a receptor molecule that is present on the surface of both T cells and natural killer (NK) cells is CD2 and further members of the CD2-superfamily. CD2 is able to act as a co-stimulatory molecule on T and NK cells.

In some embodiments, the first binding site of the anti-body molecule binds a RSV antigen and the second binding site binds a T cell specific receptor molecule and/or a natural killer (NK) cell specific receptor molecule.

In some embodiments, the first binding site of the anti-body molecule binds one of RSV antigen selected from RSV-F, RSV-G, RSV-Ga, RSV-Gb, RSV-M2-1, or RSV M2-2 or a polyprotein comprising any combination thereof, and the second binding site binds a T cell specific receptor molecule and/or a natural killer (NK) cell specific receptor molecule. In some embodiments, the first binding site of the antibody molecule binds a RSV antigen and the second binding site binds one of CD3, the T cell receptor (TCR), CD28, CD16, NKG2D, Ox40, 4-1BB, CD2, CD5 and CD95.

In some embodiments, the first binding site of the anti-body molecule binds a T cell specific receptor molecule and/or a natural killer (NK) cell specific receptor molecule and the second binding site binds a RSV antigen. In some embodiments, the first binding site of the antibody binds a T cell specific receptor molecule and/or a natural killer (NK) cell specific receptor molecule and the second binding site binds one of RSV-F, RSV-G, RSV-Ga, RSV-Gb, RSV-M2-1, or RSV M2-2, or a polyprotein comprising any combination thereof. In some embodiments, the first binding site of the antibody binds one of CD3, the T cell receptor (TCR), CD28, CD16, NKG2D, Ox40, 4-1BB, CD2, CD5 and CD95, and the second binding site binds an RSV antigen.

Bifunctional Antibody

The recombinant nucleic acid sequence can encode a bifunctional antibody, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via comple-ment-mediated lysis (CML).

Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a seine residue in the CH2 domain with a threonine residue, a threonine residue in the CH2 domain with a glutamate residue, or any combination thereof, thereby extending the half-life of the antibody.

Defucosylation

The recombinant nucleic acid sequence can encode an antibody that is not fucosylated (i.e., a defucosylated anti-body or a non-fucosylated antibody), a fragment thereof, a variant thereof, or a combination thereof. Fucosylation includes the addition of the sugar fucose to a molecule, for example, the attachment of fucose to N-glycans, 0-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof.

The modification may be one or more amino acid substitutions in the heavy chain, one or more amino acid substitutions in the light chain, or a combination thereof.

Reduced ADE Response

The antibody may be modified to reduce or prevent antibody-dependent enhancement (ADE) of disease associated with the antigen, but still neutralize the antigen.

In some embodiments, the antibody may be modified to include one or more amino acid substitutions that reduce or prevent binding of the antibody to FcγR1a. The one or more amino acid substitutions may be in the constant region of the antibody. The one or more amino acid substitutions may include replacing a leucine residue with an alanine residue in the constant region of the antibody, i.e., also known herein as LA, LA mutation or LA substitution. The one or more amino acid substitutions may include replacing two leucine residues, each with an alanine residue, in the constant region of the antibody and also known herein as LALA (SEQ ID NO:8), LALA (SEQ ID NO:8) mutation, or LALA (SEQ ID NO:8) substitution. The presence of the LALA (SEQ ID NO:8) substitutions may prevent or block the antibody from binding to FcγR1a, and thus, the modified antibody does not enhance or cause ADE of disease associated with the antigen, but still neutralizes the antigen.

Monoclonal Antibodies

In one embodiment, the invention provides anti-RSV antibodies. The antibodies may be intact monoclonal antibodies, and immunologically active fragments (e.g., a Fab or (Fab)₂ fragment), a monoclonal antibody heavy chain, or a monoclonal antibody light chain.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

In one embodiment, the anti-RSV antibody comprises an amino acid sequence at least 90% homologous to the amino acid sequence encoded by one of SEQ ID NOs: 1-6, or a fragment of an amino acid sequence at least 90% homologous to the amino acid sequence encoded by one of SEQ ID NOs: 1-6. In one embodiment, the anti-RSV antibody comprises an amino acid sequence at least 90% homologous to SEQ ID NO; 7, or a fragment of an amino acid sequence at least 90% homologous to SEQ ID NO:7. In one embodiment, the anti-RSV antibody comprises the amino acid sequence encoded by one of SEQ ID NOs: 1-6, or a fragment of the amino acid sequence encoded by one of SEQ ID NOs: 1-6. In one embodiment, the anti-RSV antibody comprises the amino acid sequence set forth in SEQ ID NO:7, or a fragment of the amino acid sequence set forth in SEQ ID NO:7.

5. ANTIGEN

The synthetic antibody is directed to the antigen or fragment or variant thereof. The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

The antigen can be from a virus. The antigen can be associated with viral infection. In one embodiment, the antigen can be associated with Respiratory Syncytial virus infection. In one embodiment, the antigen can be an RSV glycoprotein or RSV structural protein. In one embodiment, the RSV antigen can be RSV-F, RSV-G, RSV-Ga, RSV-Gb, RSV-M2-1, or RSV M2-2.

In one embodiment, the antigen can be a fragment of an RSV protein. In one embodiment, the antigen can be a fragment of an RSV glycoprotein or RSV structural protein.

In one embodiment, a synthetic antibody of the invention targets two or more antigens. In one embodiment, at least one antigen of a bispecific antibody is selected from the antigens described herein. In one embodiment, the two or more antigens are selected from the antigens described herein.

Viral Antigens

The viral antigen can be a viral antigen or fragment or variant thereof. The virus can be a disease-causing virus. The virus can be a Respiratory Syncytial virus.

The antigen may be a RSV antigen, or fragment thereof, or variant thereof. The RSV antigen can be from a factor that allows the virus to replicate, infect or survive. Factors that allow RSV to replicate or survive include, but are not limited to structural proteins and non-structural proteins. Such a protein can be a glycoprotein, structural protein or non-structural protein. In one embodiment, the RSV antigen can include RSV-G, RSV-F, RSV-SH, RSV-N, RSV-P, RSV-M, and RSV-L.

6. EXCIPIENTS AND OTHER COMPONENTS OF THE COMPOSITION

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Ser. No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

7. METHOD OF GENERATING THE SYNTHETIC ANTIBODY

The present invention also relates a method of generating the synthetic antibody. The method can include administering the composition to the subject in need thereof by using the method of delivery described in more detail below. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

8. METHOD OF IDENTIFYING OR SCREENING FOR THE ANTIBODY

The present invention further relates to a method of identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody.

9. METHOD OF DELIVERY OF THE COMPOSITION

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intranasal, intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.
Electroporation Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application Ser. No. 11/874,072, filed Oct. 17, 2007, which claims the benefit under 35 USC 119(e) to U.S. Provisional Applications Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments, that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

10. METHOD OF TREATMENT

Also provided herein is a method of treating, protecting against, and/or preventing disease in a subject in need thereof by generating the synthetic antibody in the subject. The method can include administering the composition to the subject. Administration of the composition to the subject can be done using the method of delivery described above.

In certain embodiments, the invention provides a method of treating protecting against, and/or preventing a RSV infection. In one embodiment, the method treats, protects against, and/or prevents a disease associated with RSV.

Upon generation of the synthetic antibody in the subject, the synthetic antibody can bind to or react with the antigen. Such binding can neutralize the antigen, block recognition of the antigen by another molecule, for example, a protein or nucleic acid, and elicit or induce an immune response to the antigen, thereby treating, protecting against, and/or preventing the disease associated with the antigen in the subject.

The synthetic antibody can treat, prevent, and/or protect against disease in the subject administered the composition. The synthetic antibody by binding the antigen can treat, prevent, and/or protect against disease in the subject administered the composition. The synthetic antibody can promote survival of the disease in the subject administered the composition. In one embodiment, the synthetic antibody can provide increased survival of the disease in the subject over the expected survival of a subject having the disease who has not been administered the synthetic antibody. In various embodiments, the synthetic antibody can provide at least about a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or a 100% increase in survival of the disease in subjects administered the composition over the expected survival in the absence of the composition. In one embodiment, the synthetic antibody can provide increased protection against the disease in the subject over the expected protection of a subject who has not been administered the synthetic antibody. In various embodiments, the synthetic antibody can protect against disease in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of subjects administered the composition over the expected protection in the absence of the composition.

The composition dose can be between 1 µg to 10 mg active component/kg body weight/time, and can be 20 µg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

11. USE IN COMBINATION WITH ANTIBIOTICS

The present invention also provides a method of treating, protecting against, and/or preventing disease in a subject in need thereof by administering a combination of the synthetic antibody and a therapeutic antibiotic agent.

The synthetic antibody and an antibiotic agent may be administered using any suitable method such that a combination of the synthetic antibody and antibiotic agent are both present in the subject. In one embodiment, the method may comprise administration of a first composition comprising a synthetic antibody of the invention by any of the methods described in detail above and administration of a second composition comprising an antibiotic agent less than 1, less than 2, less than 3, less than 4, less than 5, less than 6, less than 7, less than 8, less than 9 or less than 10 days following administration of the synthetic antibody. In one embodiment, the method may comprise administration of a first composition comprising a synthetic antibody of the invention by any of the methods described in detail above and administration of a second composition comprising an antibiotic agent more than 1, more than 2, more than 3, more than 4, more than 5, more than 6, more than 7, more than 8, more than 9 or more than 10 days following administration of the synthetic antibody. In one embodiment, the method may comprise administration of a first composition comprising an antibiotic agent and administration of a second composition comprising a synthetic antibody of the invention by any of the methods described in detail above less than 1, less than 2, less than 3, less than 4, less than 5, less than 6, less than 7, less than 8, less than 9 or less than 10 days following administration of the antibiotic agent. In one embodiment, the method may comprise administration of a first composition comprising an antibiotic agent and administration of a second composition comprising a synthetic antibody of the invention by any of the methods described in detail above more than 1, more than 2, more than 3, more than 4, more than 5, more than 6, more than 7, more than 8, more than 9 or more than 10 days following administration of the antibiotic agent. In one embodiment, the method may comprise administration of a first composition comprising a synthetic antibody of the invention by any of the methods described in detail above and a second composition comprising an antibiotic agent concurrently. In one embodiment, the method may comprise administration of a first composition comprising a synthetic antibody of the invention by any of the methods described in detail above and a second composition comprising an antibiotic agent concurrently. In one embodiment, the method may comprise administration of a single composition comprising a synthetic antibody of the invention and an antibiotic agent.

Non-limiting examples of antibiotics that can be used in combination with the synthetic antibody of the invention include aminoglycosides (e.g., gentamicin, amikacin, tobramycin), quinolones (e.g., ciprofloxacin, levofloxacin), cephalosporins (e.g., ceftazidime, cefepime, cefoperazone, cefpirome, ceftobiprole), antipseudomonal penicillins: carboxypenicillins (e.g., carbenicillin and ticarcillin) and ureidopenicillins (e.g., mezlocillin, azlocillin, and piperacillin), carbapenems (e.g., meropenem, imipenem, doripenem), polymyxins (e.g., polymyxin B and colistin) and monobactams (e.g., aztreonam).

12. GENERATION OF SYNTHETIC ANTIBODIES IN VITRO AND EX VIVO

In one embodiment, the synthetic antibody is generated in vitro or ex vivo. For example, in one embodiment, a nucleic acid encoding a synthetic antibody can be introduced and expressed in an in vitro or ex vivo cell. Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

13. EXAMPLES

The present invention is further illustrated in the following Examples. It should be understood that these Examples, while indicating preferred embodiments, of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

The data presented herein demonstrates an antibody gene delivery platform employing an engineered anti-RSV-F DNA-encoded monoclonal antibody (dMAb) which can overcome many of the hurdles which have limited the global use of recombinant monoclonal antibodies (mAb) as prophylactics to target infectious disease. In vivo delivery of this antibody construct gene resulted in robust systemic levels of the antibody in the serum in experimental animal models. In cotton rats, which are the gold-standard animals to model RSV infection, sustained serum-expression of the dMAb and the presence of the antibody in lung-lavage samples was observed, demonstrating the potential for long lasting immunity and effective biodistribution. Furthermore, serum from animals harboring RSV-F dMAb was functionally active in terms of antigen binding and neutralizing live virus, and the RSV-F dMAb conferred protection against disease challenge. Importantly, this RSV-F dMAb provided protection from lower respiratory illness in a live virus challenge study in the gold standard animal surrogate for modeling human RSV infection which is the cotton rat. These findings support the significance of dMAb as a potential platform technology to widen global access to monoclonal antibody-based immunoprophylactic agents and tackle the burden of infectious disease.

The materials and methods are now described.

Animals

Female Balb/c mice between 4 and 6 weeks of age and cotton rats between 6 and 8 weeks of age were group-housed with ad libitum access to feed and water.

Animal Treatments

Mice and cotton rats were shaved over the muscles of their hind legs. RSV-F dMAb plasmid DNA was formulated with 117.8-128.5 U/ml of human recombinant hyaluronidase (Hylenex®, Halozyme, San Diego, CA). Mice received 30 μl and cotton rats 200 μl intramuscular (IM) injections of formulation. Injection depth was controlled for 2 mm in mice and 5 mm in cotton rats. EP was delivered at the injection site with the CELLECTRA-3P®. An array of three needle electrodes with 3 mm insertion depth was used for mice and 6 mm depth for cotton rats. The EP treatment consists of two sets of pulses with 0.1 Amp constant current. Second pulse sets is delayed 3 seconds. Within each set there are two 52 ms pulses with a 198 ms delay between the pulses.

Immunofluorescence Staining 7 days after IM delivery of pDNA cotton rat and mice muscle tissue was harvested, fixed in 10% Neutral-buffered Formalin (BBC Biochemical, Stanford, MA) and immersed in 30% (w/v) sucrose (Sigma, Saint Louis, MO) in D.I.water for in vivo staining of dMAb expression. Tissues were then embedded into O.C.T. compound (Sakura Finetek, Torrance, CA) and snap-frozen. Frozen tissue blocks were sectioned to a thickness of 18 μm.

For in vitro staining of dMAb expression transfected 293T cells were cultured on chamber slides and fixed 3 days after transfection with 10% Neutral-buffered Formalin (BBC Biochemical) for 10 minutes at room temperature and then washed with PBS.

Slides were incubated with Blocking-Buffer (0.3% (v/v) Triton-X (Sigma), 2% (v/v) donkey serum in PBS) for 30 min, covered with Parafilm. Goat anti-human IgG-Fc fragment antibody (Bethyl, Montgomery, TX) was diluted 1:100 in incubation buffer (1% (w/v) BSA (Sigma), 2% (v/v) donkey serum, 0.3% (v/v) Triton-X (Sigma) and 0.025% (v/v) lg/ml Sodium Azide (Sigma) in PBS).150 μl of staining solution was added to each slide and incubated for 2 hrs. Slides were washed 5 minutes in 1×PBS three times. Donkey anti-goat IgG AF488 (Abcam, Cambridge, UK) was diluted 1:200 in incubation buffer and 50 μl was added to each section. Slides were washed after 1 hour incubation and mounted with DAPI-Fluoromount (SouthemBiotech, Birmingham, AL) and covered.

In vivo and in vitro expression of dMAb constructs was imaged with a BX51 Fluorescent microscope (Olympus, Center Valley, PA) equipped with Retiga3000 monochromatic camera (QImaging, Surrey, Canada).

SDS-PAGE and Western Blot

Lipofectamine 3000 transfection kit (ThermoFisher, Waltham, MA) was used to transfect adherent HEK 293T cells (ATCC® CRL11268™) with plasmids encoding for human RSV IgG and sc-Fv-Fc RSV-dMAb. Media was harvested 72 hrs post transfection and filtered using 0.22 μm stericup-GP vacuum filtration system (Millipore, Burlington, MA). The supernatant from sc-Fv-Fc RSV dMAb transfected cells was purified using Protein A spin columns (ThermoFisher) by manufacturer's instructions. The eluted protein was concentrated by Amicon Ultra-15 Centrifugal Filter unit (30 kDa) and quantified by Nanodrop. The supernatant from human RSV IgG transfected cells was purified using Protein G GraviTrap (GE Healthcare, Chicago, IL) by manufacturer's instructions. The eluted protein was concentrated by Amicon Ultra-15 Centrifugal Filter unit (30 kDa). 10 μg of each sample were loaded on a NuPAGE™ 4-12% Bis-Tris gel (ThermoFisher). Precision Plus Protein Kaleidoscope Prestained Protein Standard (Bio-Rad, Hercules, CA) was used as the standard marker. The gel was transferred to PVDF membrane using iBlot™ 2 Transfer device (Invitrogen, Waltham, MA). The membrane was blocked with goat histology buffer (1% (w/v) BSA (Sigma), 2% (v/v) goat serum (Sigma), 0.3% (v/v) Triton-X (Sigma) and 0.025% (v/v) lg/ml Sodium Azide (Sigma) in PBS) for 30 minutes at room temperature. Goat anti-Human IgG-heavy and light chain monkey-adsorbed Antibody HRP Conjugated (A80-319P, Bethyl) in 1:5000 dilution in goat histology buffer was added and incubated for 1 hour at room temperature. After washing the blot for 5 minutes in 1×DPBS (HyClone, Logan, UT) three times, goat anti-Human IgG-Fc Fragment Antibody HRP (A80-104P, Bethyl) in 1:5000 dilution in goat histology buffer was added and incubated for 1 hour at room temperature. After washing the blot for 5 minutes in 1×DPBS three times, the membrane was developed using ECL™ Prime Western Blotting system (GE Healthcare) and imaged using Protein Simple FluorChem System.

Quantification of Human RSV-F dMAb in Animal Serum and BAL 96-well assay plates (Thermo Scientific) were coated with lug/well goat anti-huIgG Fc fragment antibody (Bethyl) in 1×DPBS (ThermoFisher) overnight at 4° C. Next day plates were washed with 0.2% (v/v)TWEEN in 1×PBS wash buffer and blocked with 10%(v/v)FBS in 1×DPBS for 1 hour at room temperature. The serum samples were diluted in 1% (v/v) FBS in 0.2% (v/v) TWEEN-1×PBS and 100 μl of this mix was added to the washed assay plate. Additionally standard dilutions of purified human single chain antibody was prepared as 1:2 serial dilutions starting at 500 ng/ml in dilution buffer and added in duplicates to each assay plate. Samples and standard were incubated for 1 hour at room temperature. After washing, the plates were incubated with a 1:10,000 dilution Goat anti-Human IgG-Fc Fragment Antibody HRP (Bethyl, A80-104P) for 1 hour at room temperature. For detection SureBlue Substrate solution (Seracare, Milford, MA) was added to the washed plates. The reaction was stopped by adding TMB Stop Solution (Seracare, Milford, MA) after 6 minutes to the assay plates. The O.D. were read at 450 nm. The serum-level expression was interpolated from the standard curve using a sigmoidal four parameter logistic curve fit for log of the concentration.

Antigen Binding ELISA

Assay plates were coated with 1 μg/well of human respiratory syncytial virus (RSV) (A2) Fusion glycoprotein (Sino Biological, Wayne, PA) diluted in 1×DPBS (ThermoFisher) overnight at 4° C. Plates were washed with 1×PBS buffer with 0.05% TWEEN. 250 μl/well of 3% (w/v) BSA in 1×PBS with 0.05% TWEEN were added and incubated for 1 hour at room temperature. Serum samples were diluted in 1% (w/v) BSA in 1×PBS with 0.05% TWEEN. After washing the assay plates serum samples were added in threefold serial dilutions. Plates were incubated 1 hour at room temperature. After washing 100 μl of 1:10000 diluted Goat anti-Human IgG-Fc Fragment Antibody HRP (Bethyl, A80-104P) was added and incubated for 1 hour at room temperature. For development the SureBlue/TMB Stop Solution (Seracare, Milford, MA) was used and O.D. was recorded at 450 nm.

RSV Neutralizing Antibody Assay (60% Reduction)

Heat-treated sera samples were diluted 1:10 with EMEM and serially diluted further 1:4. Diluted sera samples were incubated with RSV (25-50 PFU) for 1 hour at room temperature and inoculated in duplicates onto confluent HEp-2 monolayers in 24 well plates. After one hour incubation at 37° C. in a 5% $CO_2$ incubator, the wells were overlaid with 0.75% Methylcellulose medium. After 4 days of incubation the overlay was removed and the cells were fixed with 0.1% crystal violet stain for one hour and then rinsed and air dried. The corresponding reciprocal neutralizing antibody titers were determined at the 60% reduction end-point of the virus control using the statistics program. The geometric means±standard error for all animals in a group were calculated.

Cotton Rat Challenge Study

Animals:

Fifteen (15) inbred female *Sigmodon hispidus* cotton rats between 6 and 8 weeks of age (Source: Sigmovir Biosystems, Inc., Rockville MD) were maintained and handled under veterinary supervision in accordance with National Institutes of Health guidelines and Sigmovir Institutional Animal Care and Use Committee's approved animal study protocol. The cotton rats were housed in clear polycarbonate cages individually and provided with standard rodent chow (Harlan #7004) and tap water ad lib.

Challenge Virus:

The prototype Long strain of RSV/A (ATCC, Manassas, VA) was propagated in HEp-2 cells after serial plaque-purification to reduce defective-interfering particles. A pool of virus designated as hRSV/A/Long Lot #021413, prepared in sucrose stabilizing media, and containing approximately $2\times10^7$ pfu/ml was used for this in vivo experiment. This stock of virus is stored under −80° C. condition and has been characterized in vivo using the cotton rat model for upper and lower respiratory tract replication.

Procedure:

15 adult female cotton rats (6-8 weeks of age) were divided into three groups of five animals each. Animals of the RSV-dMAb group were treated as described above at day 0 of the experiment. Animals in the Palivizumab control group were injected IM with 0.1 ml of 15 mg/kg Palivizumab on day 6 of the experiment. A third group of animals remained untreated. At day 7 all animals were challenged with 105 pfu of RSV/A/Long (IN) in a 0.1 mL volume. All animals were sacrificed at day 12. The lung was harvested en bloc and tri-sected, left section was used for viral titrations and lingular lobe for qPCR.

Lung Viral Titration

Lung homogenates are clarified by centrifugation and diluted in EMEM. Confluent HEp-2 monolayers are infected in duplicates with diluted homogenates in 24 well plates. After one hour incubation at 37° C. in a 5% $CO_2$ incubator, the wells are overlaid with 0.75% Methylcellulose medium. After 4 days of incubation, the overlay is removed and the cells are fixed with 0.1% crystal violet stain for one hour and then rinsed and air dried. Plaques are counted and virus titer is expressed as plaque forming units per gram of tissue. Viral titers are calculated as geometric mean+standard error for all animals in a group at a given time.

Real-Time PCR of Lung Tissue

Total RNA is extracted from homogenized lung tissue using the RNeasy purification kit (QIAGEN, Valencia, CA). One µg of total RNA is used to prepare cDNA using Super Script II RT (Invitrogen) and oligo dT primer (1 µl, Invitrogen). For the real-time PCR reactions the Bio-Rad iQ™ SYBR Green Supermix is used in a final volume of 25 µl, with final primer concentrations of 0.5 µM. Reactions are set up in duplicates in 96-well trays. Amplifications are performed on a Bio-Rad iCycler for 1 cycle of 95° C. for 3 min, followed by 40 cycles of 95° C. for 10 s, 60° C. for 10 s, and 72° C. for 15 s. The baseline cycles and cycle threshold (Ct) are calculated by the iQ5 software in the PCR Base Line Subtracted Curve Fit mode. Relative quantitation of DNA is applied to all samples. The standard curves are developed using serially-diluted cDNA sample most enriched in the transcript of interest (e.g., lungs from day 4 post-primary RSV infection). The Ct values are plotted against $\log_{10}$ cDNA dilution factor. These curves are used to convert the Ct values obtained for different samples to relative expression units. These relative expression units are then normalized to the level of b-actin mRNA ("housekeeping gene") expressed in the corresponding sample. For animal studies, mRNA levels are expressed as the geometric mean+SEM for all animals in a group at a given time.

Statistics

Statistical analysis was performed with GraphPad Prism v.7 using nonparametric two-tailed Mann-Whitney t-test.

The results are now described.

RSV-F-dMAb Construct Design

The anti-RSV-F dMAb was based on the FDA-approved anti-RSV mAb, Palivizumab. To assist in molecule design, models of the dMAb in both variable fragment (Fv) and single chain variable fragment (scFv) formats were generated using Discovery Studio 4.5 (Biovia, San Diego, CA). The scFv was modeled in both VH-VL and VL-VH orientations using a (G4S) 3 linker. Based on modeling results, the VL-VH orientation was chosen as it was predicted to cause the least perturbation to the scFv variable domains (FIG. 1A). The gene for the sc-Fv-Fc RSV-F dMAb (RSV-F dMAb) was cloned into a pVAX backbone and is under control of the human CMV promoter (FIG. 1B). RSV-F dMAb expression was confirmed by immunofluorescence staining of in vitro transfected 293T cells with RSV-F dMAb pDNA (FIG. 1C). The staining demonstrates cytosolic expression of the RSV-F-dMAb. Secretion of the RSV-F dMAb by 293T cells was confirmed by Western-Blot analysis of cell-culture supernatant (FIG. 1D). As expected, 2 bands were observed for the Palivizumab-IgG representing heavy (57 kDa) and light chain (26 kDa), and a single band (60 kDa) was detected for the single chain RSV-F dMAb construct.

dMAb In Vivo Expression Model

Figure 2:
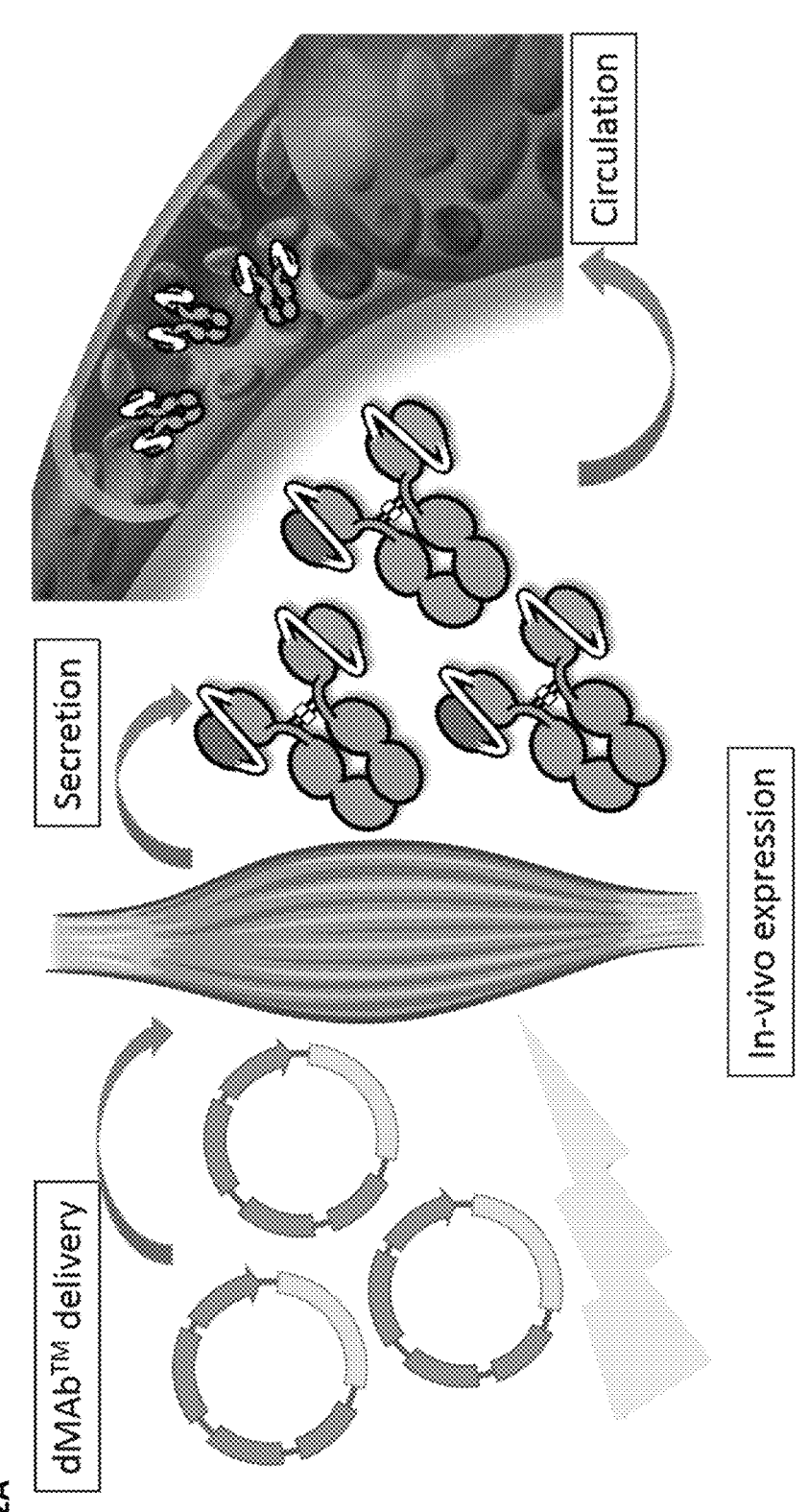
FIG. 2, comprising
Figure 2:
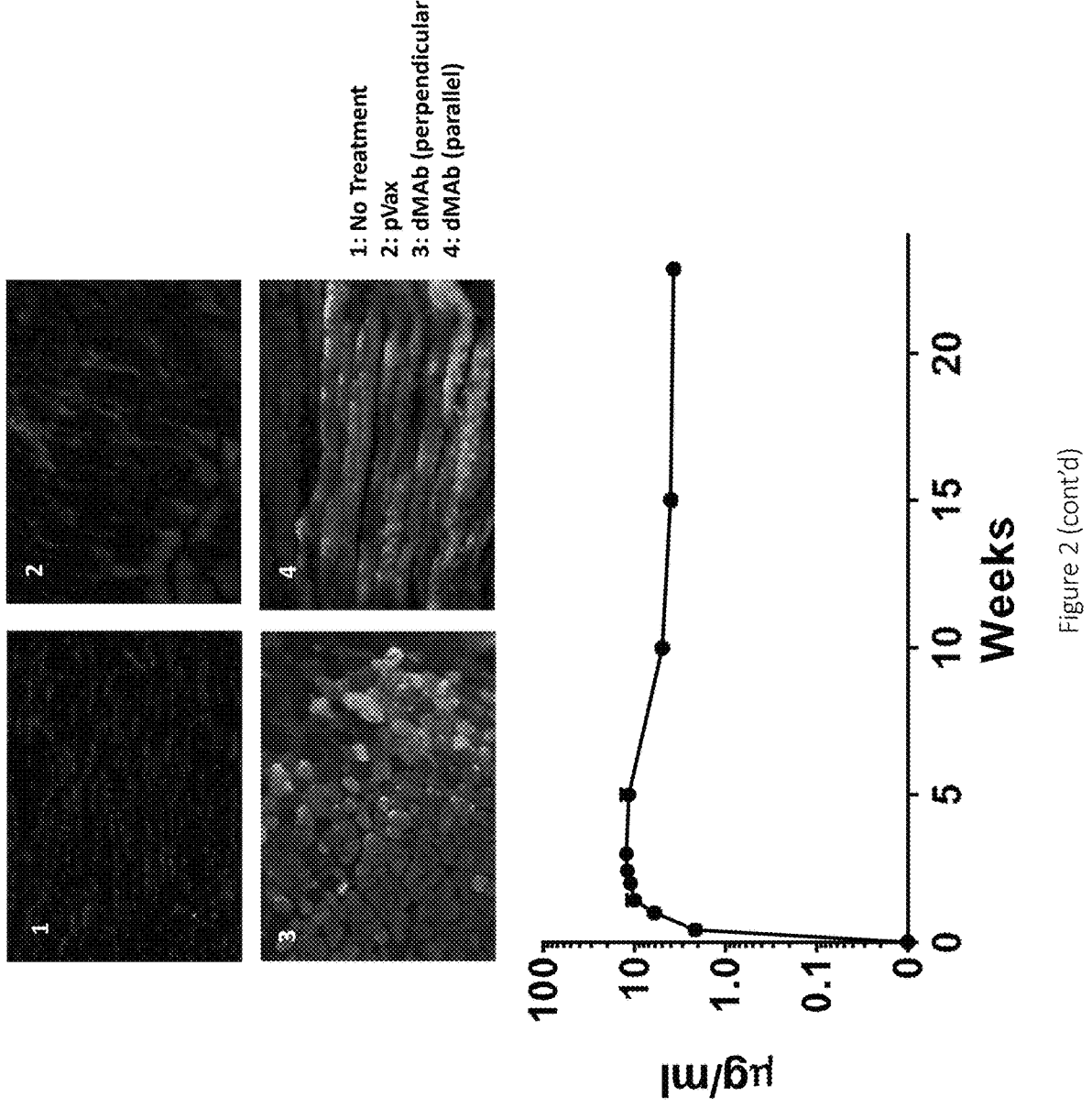

For optimal in vivo expression of dMAb an enhanced pDNA delivery protocol was developed. dMAb pDNA is formulated with the extra-cellular matrix (ECM) disrupting enzyme, hyaluronidase and delivered to the muscle with in vivo electroporation. The schematic presented in FIG. 2A outlines the dMAb platform highlighting the delivery and in vivo expression. Briefly, dMAb pDNA is delivered to the skeletal muscle with the assistance of electroporation. dMAb expression at the site of IM delivery can be visualized by staining for human IgG in myocytes (FIG. 2B). Upon production of the dMAb the myocytes secrete the antibody construct into the circulating blood volume. The dMAb can be measured in the serum (FIG. 2C). The expression of the dMAb can be sustained for months.

In Vivo Expression of RSV-F dMAbs in BALB/c Mice

Figure 3:
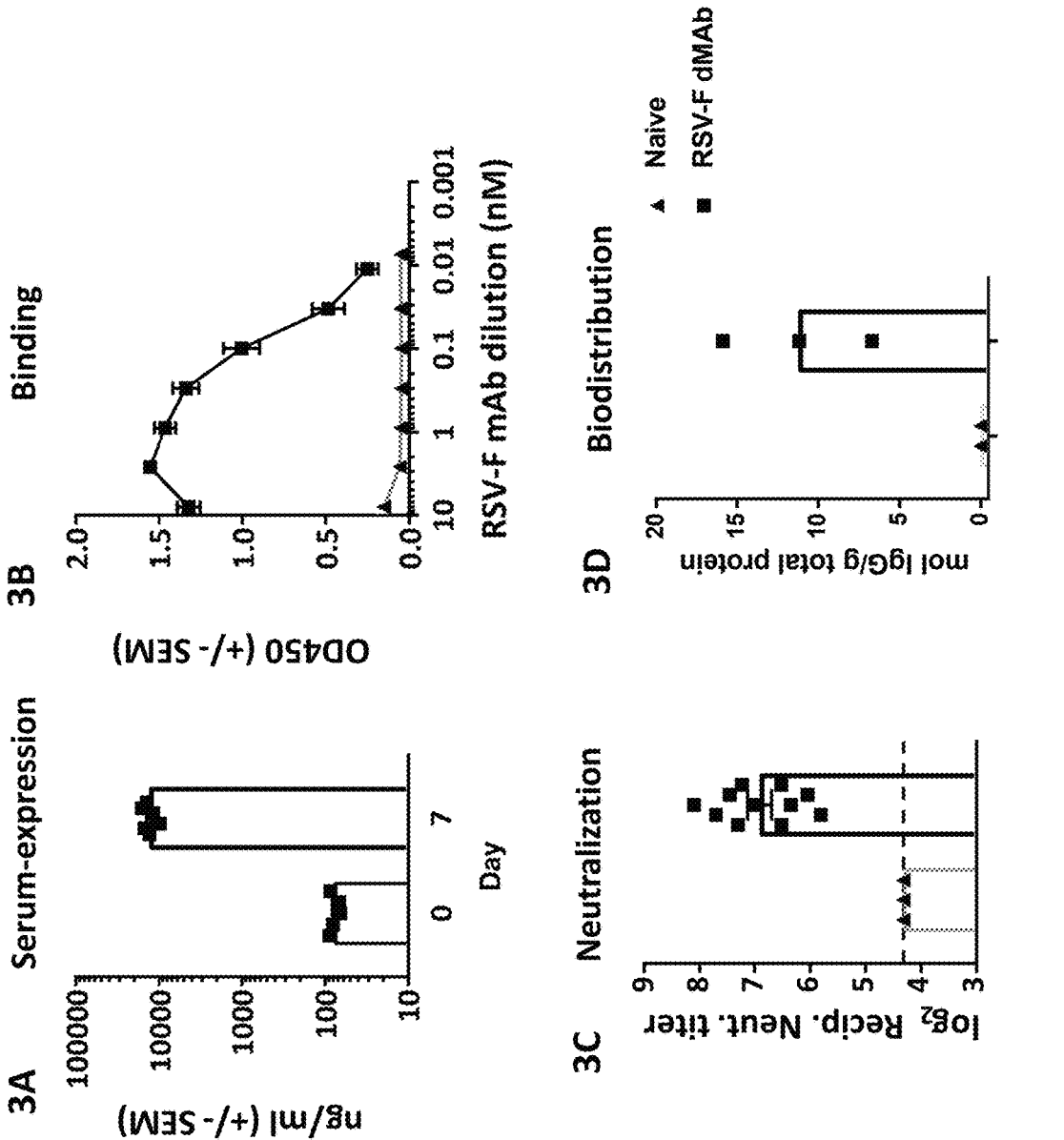
FIG. 3, comprising FIG. 3A through FIG. 3D depicts on-vivo expression of RSV-F dMAbs in Balb/c mice. RSV-F dMAb plasmid was administered to the leg muscle of Balb/c mice. Serum samples were taken 7 days after treatment.

The expression of functional RSV-F dMAbs was assessed in vivo. BALB/c mice were dosed with 50 µg of RSV-F dMAb pDNA administered to the TA muscle. The day 7 serum concentration of RSV-F dMAb averaged 7500 ng/ml (FIG. 3A). There was a decline in serum concentration after day 7 which was associated with a host anti-drug antibodies (ADA) response raised against the xenogeneic human antibody construct (data not shown). The ability of the expressed RSV-F dMAb to bind RSV-F antigen was confirmed by ELISA of serum samples from treated animals compared to untreated animals (FIG. 3B). Serum from animals treated with the RSV-dMAb construct shows a strong, serum-dilution dependent binding signal and is exhibiting a 'hook-effect' at higher serum-concentrations. RSV-F binding capability of in vivo expressed RSV-F dMAb translates into virus-neutralization functionality. Serum harboring the RSV-F-dMAb reaches robust RSV/A virus neutralizing titers of 7 $\log_2$(FIG. 3C). The biodistribution of the RSV-F dMAb to the site of RSV infection was confirmed in lung lavage samples. 7 days after RSV-F dMAb administration to the TA muscle the dMAb in bronchoalveolar lavage (BAL) samples was successfully measured, 11.25 mol mAb/g total protein+/−SEM 2.65 (FIG. 3D). In summary, IM delivery of the RSV-F dMAb resulted in the production of functional anti-RSV-F antibody construct which was present in systemic circulation and at the physiologically relevant site of natural RSV infection.

In Vivo Expression of RSV-F dMAb in Cotton Rats

Cotton rats are considered the gold standard model to model RSV infection and drug interventions. Cotton rats are susceptible to non-adapted human RSV and 100 fold more permissive than mice to infection. They also display many features of the human disease pathology[21,22].

Figure 4:
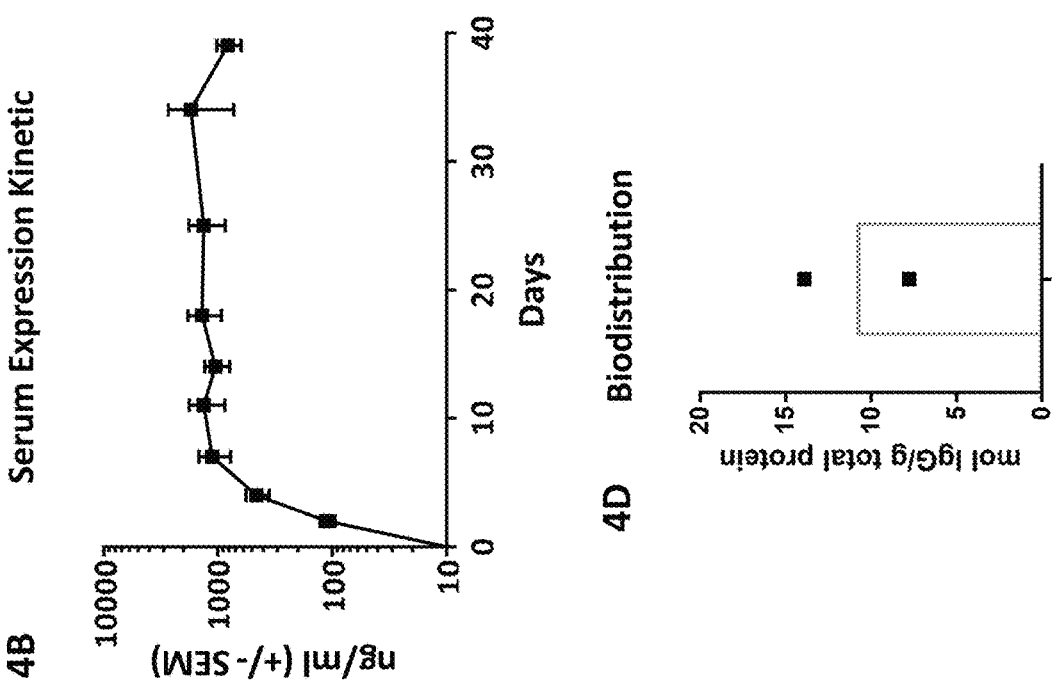
FIG. 4, comprising FIG. 4A through FIG. 4D depicts the characterization of RSV-F dMAb in cotton rats.
Figure 4:
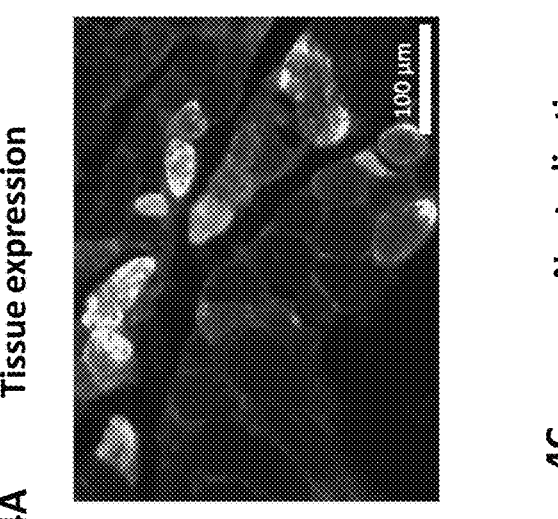
Figure 4:
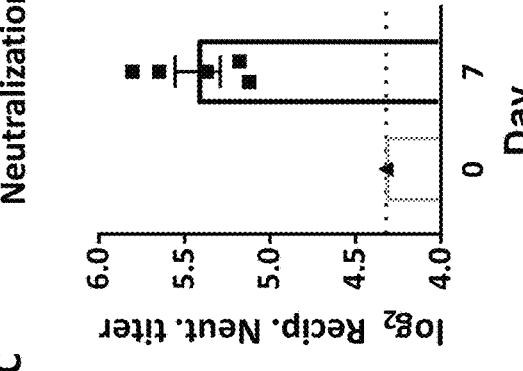

Initially the ability of cotton rat myocytes to express dMAb constructs was assessed after delivery of RSV-F dMAb pDNA to the leg muscle (FIG. 4A). Next, it was tested whether local dMAb expression led to systemic expression. Sustained (greater than 5 weeks) levels (above 1,000 ng/ml) of the RSV-F dMAb in the serum of the cotton rat were measured (FIG. 4B). The functionality of the expressed dMAb was tested in an RSV/A neutralization assay. In the plaque reduction assay an average neutralization titer of 5.4 was measured (FIG. 4C). The biodistribution of the dMAb to the site of RSV infection was assessed in BAL fluid.

Average levels of RSV-F dMAb in BAL samples from these animals was 10.8 mol/g total protein (FIG. 4D). In summary, delivery of RSV-F-dMAb pDNA to the muscles of cotton rats led to the systemic production of functional antibodies which neutralized RSV virus and were present in the lungs.

In Vivo Expressed RSV-dMAb Confers Protection from Lower Respiratory Disease

The ability to achieve functional anti-RSV-F dMAb in the cotton rat led us to test the efficacy of the platform in an active immune-prophylaxis study (FIG. 5A). Separate groups of cotton rats were either dosed with RSV-F-dMAb (group 1) or Palivizumab (group 2) or remained untreated. All groups were challenged intranasal with 105 pfu of RSV/A/Long on day 0. Five days after challenge lung tissue was harvested and viral loads measured. Both group 1 and 2 were protected from lower respiratory disease associated with RSV infection. The lungs of dMAb-treated cotton rats contained mean viral load of 250 pfu (SEM=50) 5 days after intranasal challenge. Similar viral load was measured for the lungs of Palivizumab-treated cotton rats: 200 pfu (SEM=0). In comparison lungs of untreated cotton rats contained high viral load of 27,520 pfu (SEM=8408.9) (FIG. 5B). Significantly reduced viral genome copy number in the lower respiratory tissue was measured with real-time PCR using primer targeting the Nonstructural Protein 1 (NS1) of RSV. Mean RSV-mRNA levels in dMAb-(mean RSV mRNA=0.181, SEM=0.050) and Palivizumab- (mean RSV mRNA=0.032, SEM=0.004) treated cotton rats were reduced in comparison to untreated animals (mean RSV mRNA=1.175, SEM=0.306) (FIG. 5C). Of note, dMAb-treated cotton rats were protected from Lower Respiratory disease, although RSV-F dMAb serum levels were approximately 10-fold lower than those measured for Palivizumab (FIG. 5D). In summary, these data demonstrated the ability of the AIP platform using an anti-RSV-F dMAb to protect against viral challenge in a gold standard disease model.

DMAb Protected from Lower Respiratory Disease in a Live Virus Challenge

Figure 5:
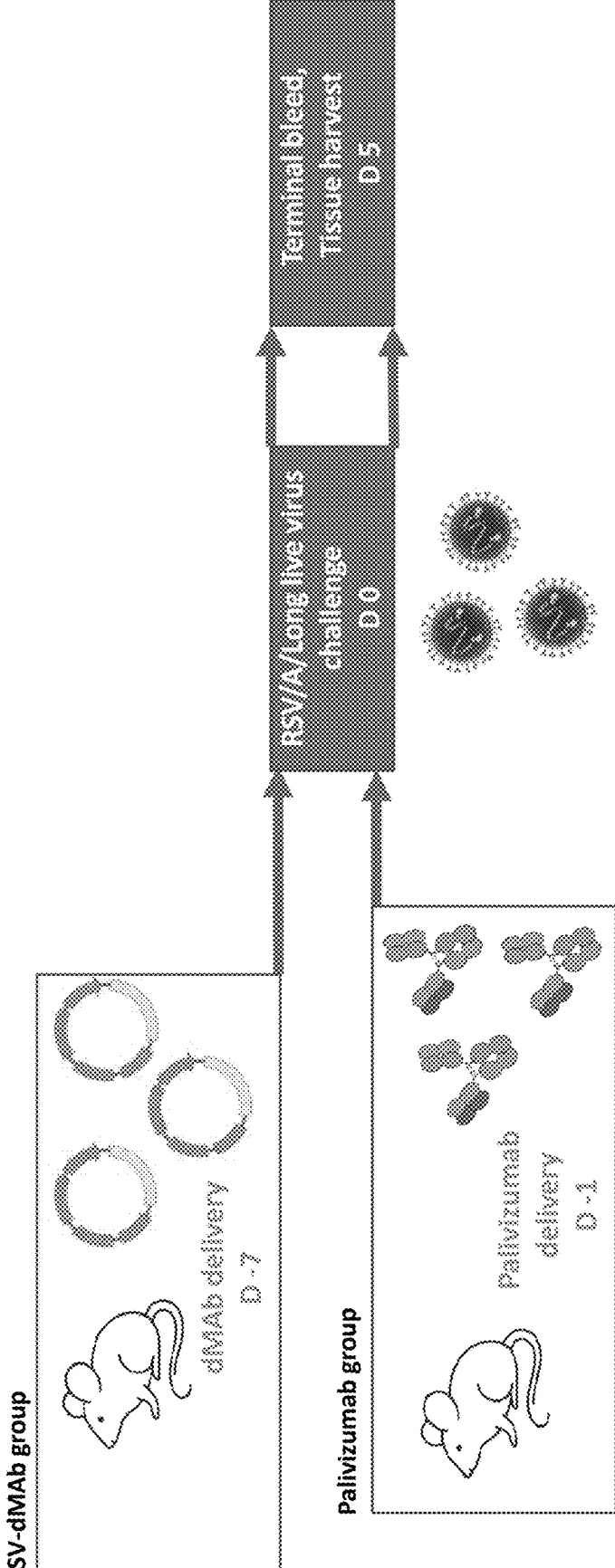
FIG. 5, comprising
Figure 5:
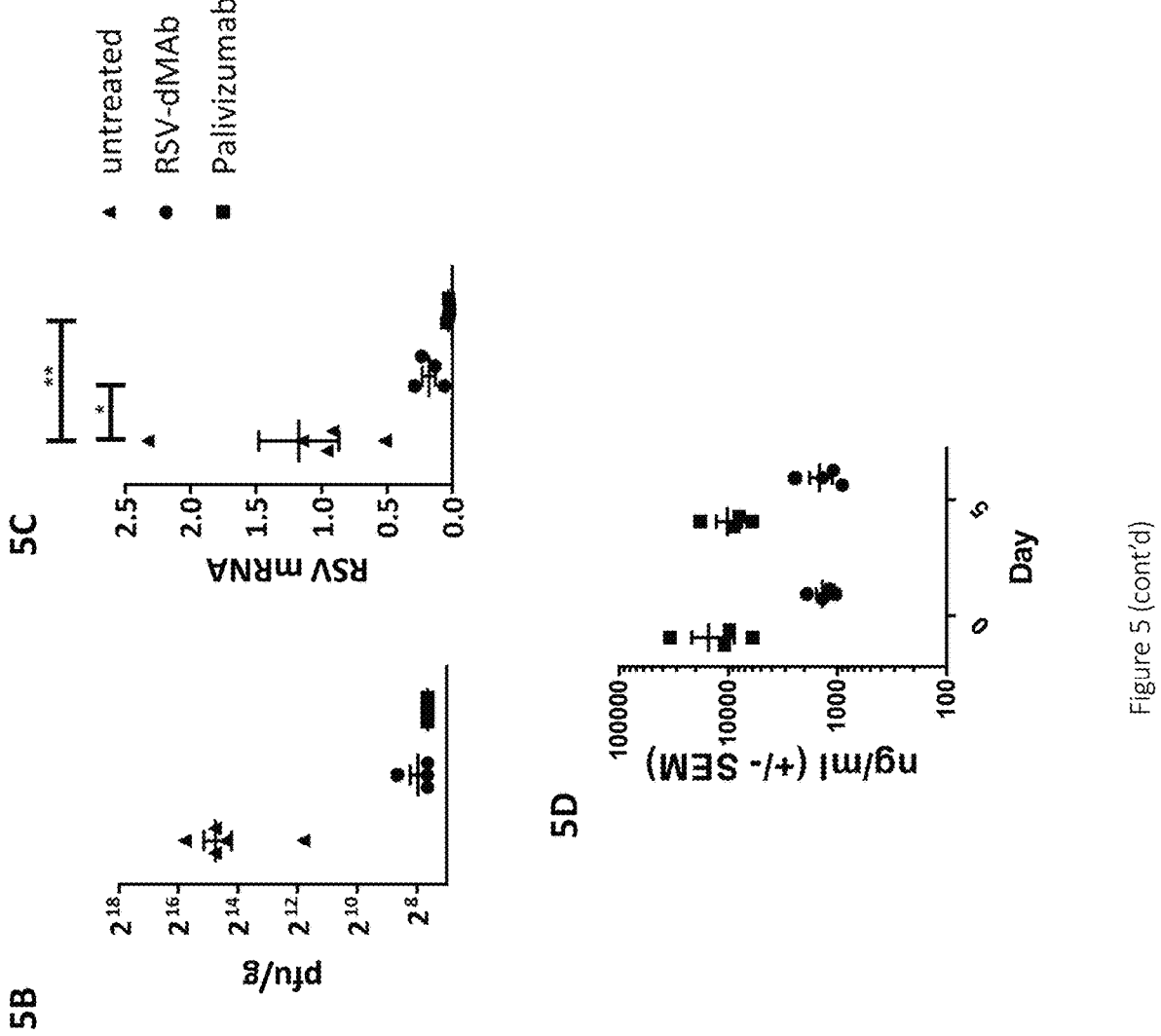
Figure 6:
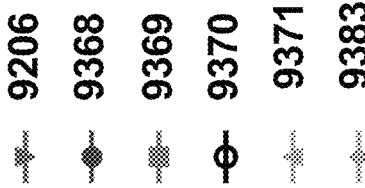
FIG. 6 depicts experimental results demonstrating the expression kinetics of RSV DMAbs.
Figure 6:
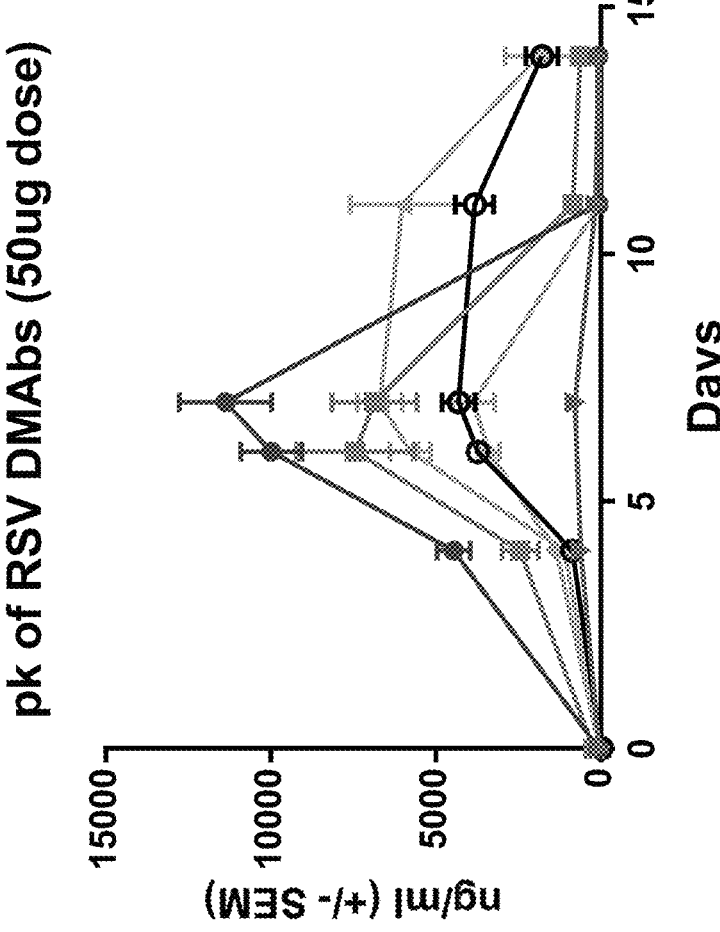
Figure 7:
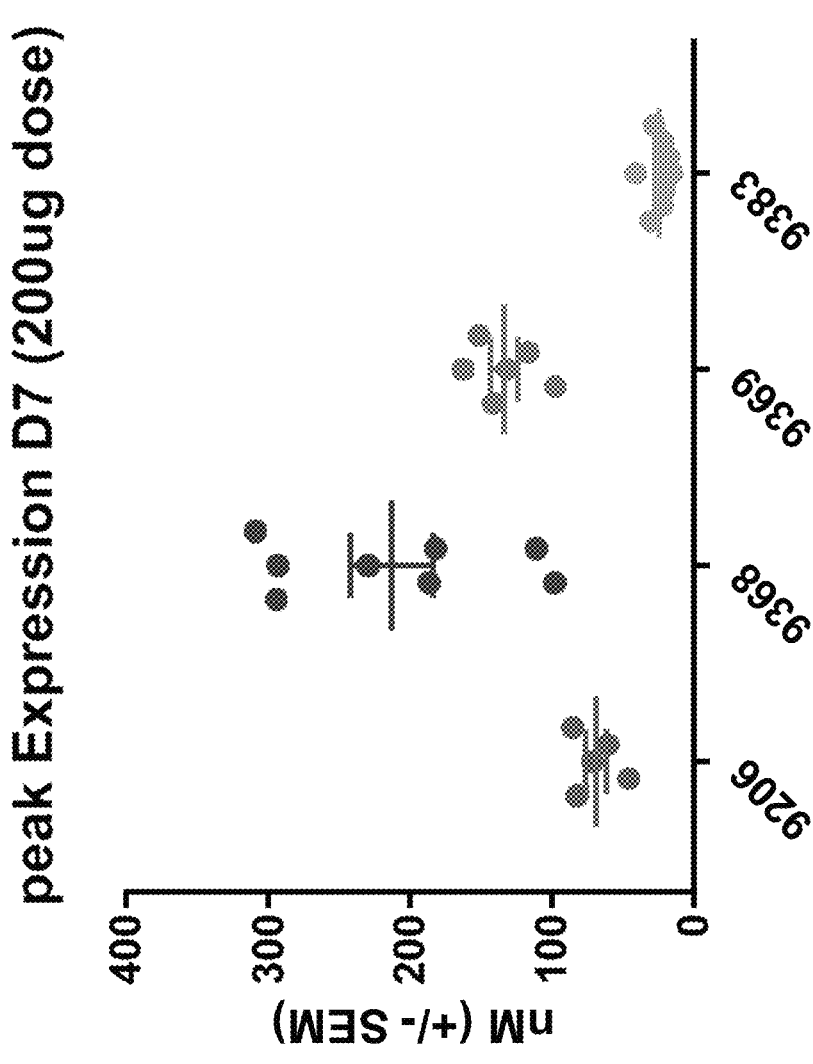
FIG. 7 depicts experimental results demonstrating the peak expression of RSV-DMAbs.
Figure 8:
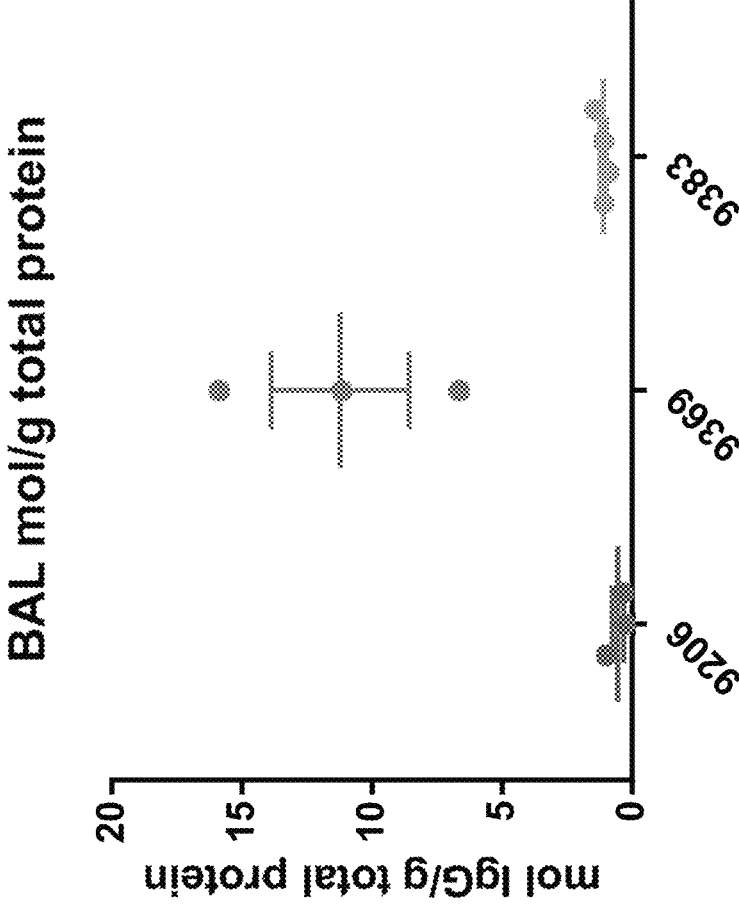
FIG. 8 depicts experimental results demonstrating amount of DMAbs in Bronchoalveolar lavage (BAL) samples.
Figure 9:
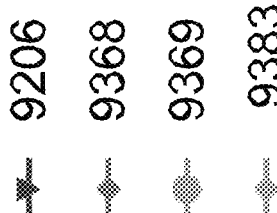
FIG. 9 depict experimental results demonstrating RSV-F binding.
Figure 9:
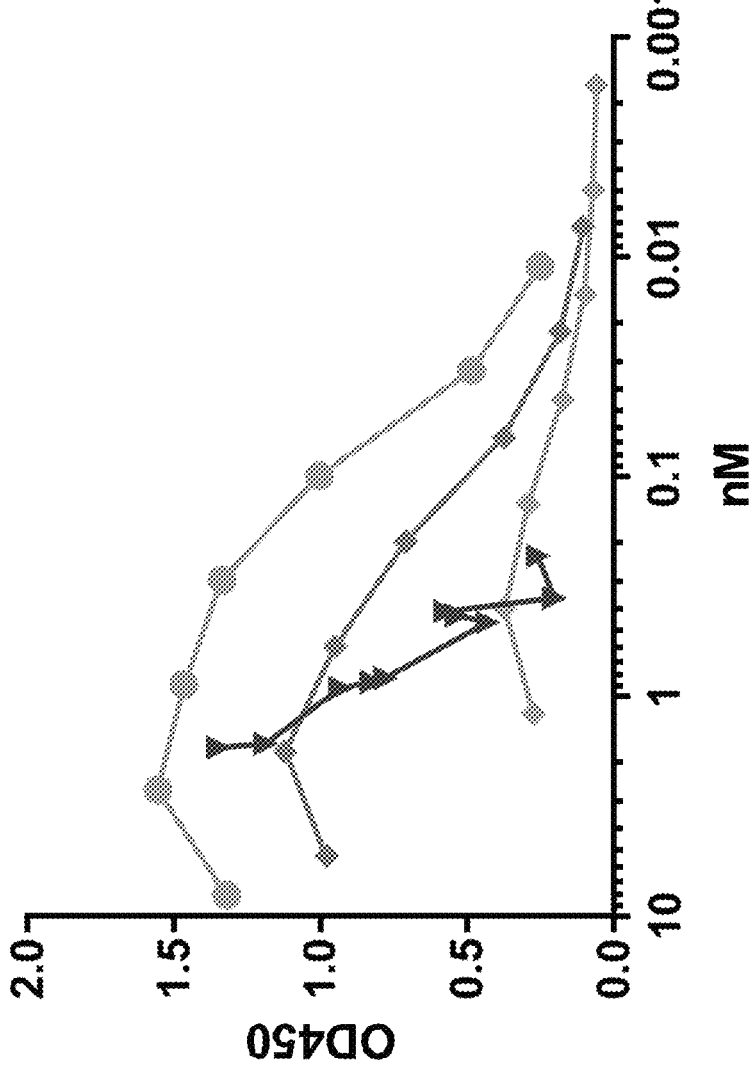
Figure 10:
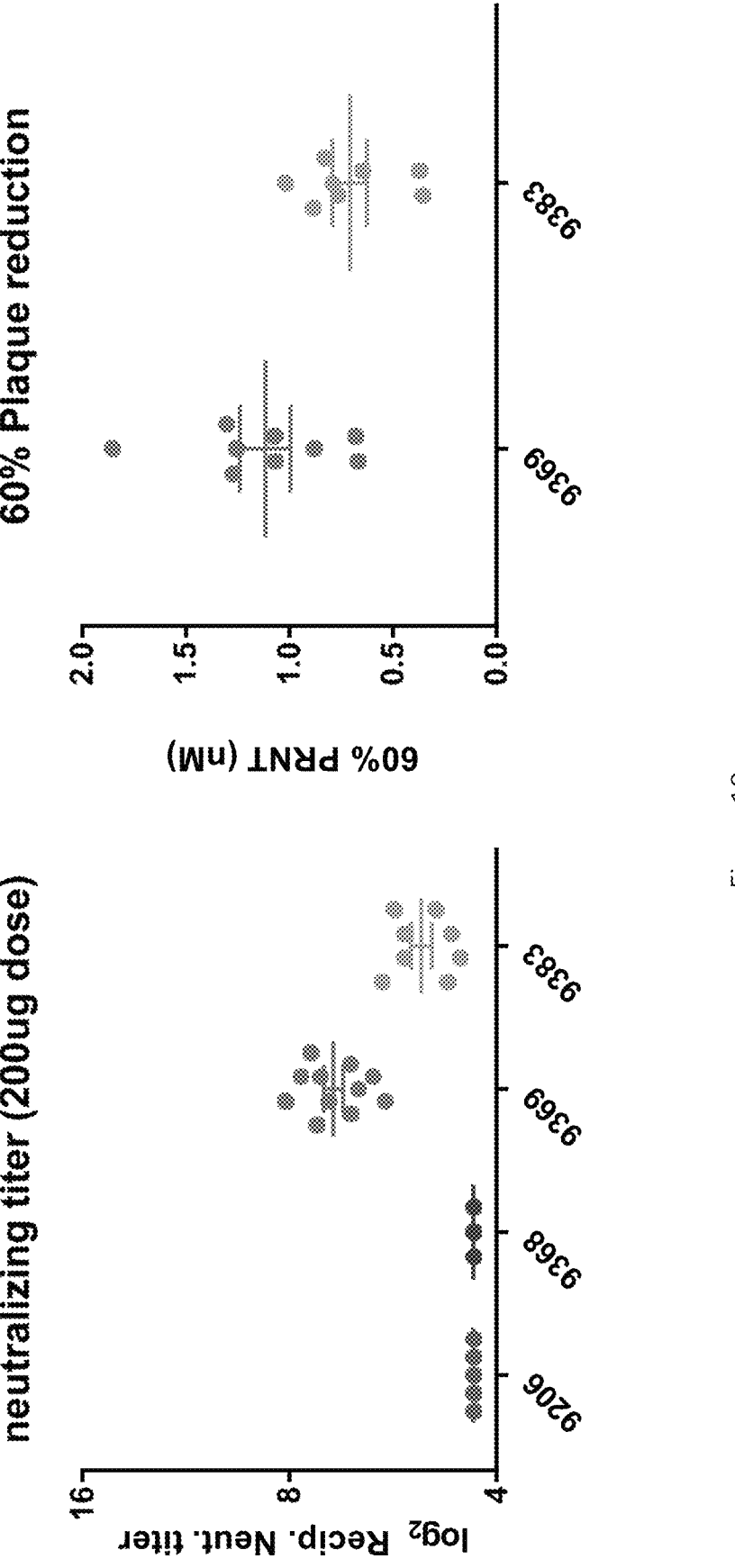
FIG. 10 depicts the experimental results demonstrating neutralization.
Figure 11:
FIG. 11 depicts the experimental results demonstrating RSV-DMAbs in the cotton rat.

There is a pressing need for the development of platform technologies which can be employed to increase patient access to prophylactic and therapeutic monoclonal antibodies. The work presented here highlights the potential of the antibody gene delivery platform, dMAb to achieve this. This is applied technology to the RSV target using a dMAb construct based on the FDA-approved mAb, Palivizumab. Data demonstrates the successful in vivo expression of the dMAb construct in multiple preclinical models and ability to confer host protection against virus challenge (FIG. 5). Data presented here and in other recent reports[10-13,23] highlight the characteristics and efficacy of the dMAb platform as a prophylactic option for a myriad of infectious diseases.

The success of dMAb technology is dependent on effective delivery of pDNA to the host. In vivo dMAb delivery targets the host myocytes in skeletal muscle, which is considered an endocrine organ, very adept at synthesize and secretion of multiple factors[24]. Furthermore, myocytes are extremely long-lived, and together these characteristics make the muscle an ideal biological factory for high level transgene expression can persist up to several months delivery[25,26]. However, to harness the full potential of the muscle site as the mAb-producing biological factory requires a highly efficient delivery of the dMAb pDNA to the myocytes. To optimize the delivery of the dMAb pDNA into the muscle EP is used and the ECM-modifying enzyme, hyaluronidase. This highlights how this delivery protocol achieves robust dMAb expression in the myocytes at the site of delivery (FIG. 2b), which leads to high levels of the dMAb secreted into circulation (FIG. 2c). Importantly, it is demonstrated that this robust expression is sustained. In the absence of an adaptive host immune response against the xenogeneic dMAb demonstrated 23-week long expression (FIG. 2C). Even in the presence of a functioning immune system in wild type cotton rats 39 days of expression were shown (FIG. 4B). Sustained expression is an extremely important component for an immune-prophylactic modality, and a characteristic which is missing with conventional recombinant mAbs. For example, administration of Palivizumab is ideally initiated prior to the RSV season onset, which typically lasts from November through April with deviation by regions[27]. It is dosed at 15 mg/kg and has to be administered monthly by intramuscular injection throughout the RSV season. The serum-half life has been reported as 20 days[28,29]. On the other hand a dMAb counterpart of Palivizumab is continuously expressed and secreted, and an efficacious circulating level of mAb in could be maintained. A single delivery of dMAb would provide protective mAbs in patient serum throughout a RSV-season. In support of this, in an extended pharmacokinetic (pK) study circulating human RSV-F dMAb levels to remain stable up to 6 weeks in cotton rats were observed (FIG. 4B) and T cell-depleted mice for months (FIG. 2C).

A characteristic of sc-Fv antibodies is their excellent biodistribution. Due to their small size they efficiently penetrate tissue. However, there effectiveness is limited by a serum half-life of just several hours. The fusion to a Fc protein increases the serum half-life of the resulting sc-Fv-Fc molecule from hours to multiple days[30]. Although it does not exceed the half-life of a full length IgG molecule, it still exhibits superior biodistribution because of its smaller size[31]. RSV-dMAb was successfully detected in the lungs of mice and cotton rats (FIGS. 3D and 4D). The increased ability of the smaller sc-Fv-Fc molecule to be present at the site of RSV-infection may explain the similar levels of protection from lower respiratory disease (FIG. 5B and FIG. 5C) despite 10 fold lower serum-concentration (FIG. 5D) compared to Palivizumab. To allow a more accurate comparison of the two molecules and their biodistribution, future experiments will be designed for both mAb constructs to be at equal concentrations in the animal serum at the time of viral challenge. The importance of biodistribution of mAbs in preventing LRD after RSV challenge was reported before. Wu et al report lower in vivo efficacy for Palivizumab-variants despite high in-vitro neutralizing ability due to poor biodistribution[32]. Tiwari et al reported promising results by targeting the lung-tissue directly for expression of mRNA-encoded RSV-Ab[33].

While other platforms have been employed to deliver antibody genes, dMAbs possess multiple advantages over other nucleic acid-based monoclonal antibody technologies, including viral vector and mRNA-based delivery of antibodies. Firstly, dMAb is a naked pDNA platform, thus it avoids anti-vector immunity which limits the use of adenovirus or recombinant adeno-associated virus based gene delivery, and no potentially toxic chemical delivery platform vehicle is required. mRNA-based mAbs generally require lipid nanoparticle-formulation[34-36]. As discussed above and highlighted in the data presented in this study there is a sustained, but finite expression profile for dMAbs. mRNA-encoded antibodies have significant shorter serum half-lives, more closely matched to those of recombinant antibodies, while adenovirus or recombinant adeno-associated virus delivery of antibody genes may lead to infinite expression, with safety concerns arising from the integration into somatic DNA and potentially unrestricted expression of the transgene[37]. Additionally, unlike many recombinant and mRNA-based antibody candidates which are delivered IV and require significant infrastructure in place to dose patients, dMAbs can be administered IM in the field. Plasmid DNA is relatively easy to manufacture, allowing for very cost-effective production. Formulated plasmid DNA is temperature stable without the need for lyophilization, and its storage and distribution does not require a cold chain.

In summary, applying the dMAb platform to target the infectious disease RSV in established disease models, this data demonstrates robust circulating levels of the RSV antibody construct in the serum and lungs of animals. Furthermore, the in vivo expressed antibody construct was functionally active and provided protection from Lower Respiratory Disease in a live virus challenge study (FIG. 5). These findings support the significance of the dMAb technology, and its potential to fight global mortality caused by infectious disease.

REFERENCES

1 Nair, H. et al. Global burden of acute lower respiratory infections due to respiratory syncytial virus in young children: a systematic review and meta-analysis. *Lancet (London, England)* 375, 1545-1555, doi:10.1016/s0140-6736(10)60206-1 (2010).

2 O'Brien, K. L. et al. Efficacy of motavizumab for the prevention of respiratory syncytial virus disease in healthy Native American infants: a phase 3 randomised double-blind placebo-controlled trial. *The Lancet. Infectious diseases* 15, 1398-1408, doi:10.1016/s1473-3099 (15)00247-9 (2015).

3 Griffin, M. P. et al. Safety, Tolerability, and Pharmacokinetics of MEDI8897, the Respiratory Syncytial Virus Prefusion F-Targeting Monoclonal Antibody with an Extended Half-Life, in Healthy Adults. *Antimicrobial agents and chemotherapy* 61, doi:10.1128/aac.01714-16 (2017).

4 Ambrose, C. S., Chen, X. & Kumar, V. R. A population-weighted, condition-adjusted estimate of palivizumab efficacy in preventing RSV-related hospitalizations among US high-risk children. *Human vaccines & immunotherapeutics* 10, 2785-2788, doi:10.4161/hv.32082 (2014).

5 Qin, Y., Guo, H., Tang, B. & Yang, S. M. The non-reverse transcriptase activity of the human telomerase reverse transcriptase promotes tumor progression (review). *International journal of oncology* 45, 525-531, doi:10.3892/ijo.2014.2470 (2014).

6 Subramanian, K. N. et al. Safety, tolerance and pharmacokinetics of a humanized monoclonal antibody to respiratory syncytial virus in premature infants and infants with bronchopulmonary dysplasia. MEDI-493 Study Group. *The Pediatric infectious disease journal* 17, 110-115 (1998).

7 Tjelle, T. E. et al. Monoclonal antibodies produced by muscle after plasmid injection and electroporation. *Molecular therapy: the journal of the American Society of Gene Therapy* 9, 328-336, doi:10.1016/j.ymthe.2003.12.007 (2004).

8 Schultheis, K. et al. in *MOLECULAR THERAPY.* 269-269 (CELL PRESS 50 HAMPSHIRE ST, FLOOR 5, CAMBRIDGE, MA 02139 USA).

9 McMahon, J. M., Signori, E., Wells, K. E., Fazio, V. M. & Wells, D. J. Optimisation of electrotransfer of plasmid into skeletal muscle by pretreatment with hyaluronidase—increased expression with reduced muscle damage. *Gene therapy* 8, 1264-1270, doi:10.1038/sj.gt.3301522 (2001).

10 Elliott, S. T. C. et al. DMAb inoculation of synthetic cross reactive antibodies protects against lethal influenza A and B infections. *NPJ Vaccines* 2, 18, doi:10.1038/s41541-017-0020-x (2017).

11 Patel, A. et al. An engineered bispecific DNA-encoded IgG antibody protects against *Pseudomonas aeruginosa* in a pneumonia challenge model. *Nat Commun* 8, 637, doi:10.1038/s41467-017-00576-7 (2017).

12 Wang, Y. et al. Anti-OspA DNA-Encoded Monoclonal Antibody Prevents Transmission of Spirochetes in Tick Challenge Providing Sterilizing Immunity in Mice. *J Infect Dis*, doi:10.1093/infdis/jiy627 (2018).

13 Muthumani, K. et al. Rapid and Long-Term Immunity Elicited by DNA-Encoded Antibody Prophylaxis and DNA Vaccination Against Chikungunya Virus. *J Infect Dis* 214, 369-378, doi:10.1093/infdis/jiw111 (2016).

14 Andrews, C. D. et al. In Vivo Production of Monoclonal Antibodies by Gene Transfer via Electroporation Protects against Lethal Influenza and Ebola Infections. *Molecular therapy. Methods & clinical development* 7, 74-82, doi:10.1016/j.omtm.2017.09.003 (2017).

15 Muthumani, K. et al. Novel prostate cancer immunotherapy with a DNA-encoded anti-prostate-specific membrane antigen monoclonal antibody. *Cancer Immunol Immunother* 66, 1577-1588, doi:10.1007/s00262-017-2042-7 (2017).

16 Hollevoet, K., De Smidt, E., Geukens, N. & Declerck, P. Prolonged in vivo expression and anti-tumor response of DNA-based anti-HER2 antibodies. *Oncotarget* 9, 13623-13636, doi:10.18632/oncotarget.24426 (2018).

17 Repp, R. et al. Combined Fc-protein- and Fc-glyco-engineering of scFv-Fc fusion proteins synergistically enhances CD16a binding but does not further enhance NK-cell mediated ADCC. *Journal of immunological methods* 373, 67-78, doi:10.1016/j.jim.2011.08.003 (2011).

18 Unverdorben, F. et al. Pharmacokinetic properties of IgG and various Fc fusion proteins in mice. *mAbs* 8, 120-128, doi:10.1080/19420862.2015.1113360 (2016).

19 Smith, T. R. F. et al. Development of an intradermal DNA vaccine delivery strategy to achieve single-dose immunity against respiratory syncytial virus. *Vaccine* 35, 2840-2847, doi:10.1016/j.vaccine.2017.04.008 (2017).

20 Coates, H. V., Alling, D. W. & Chanock, R. M. An antigenic analysis of respiratory syncytial virus isolates by a plaque reduction neutralization test. *Am J Epidemiol* 83, 299-313 (1966).

21 Prince, G. A. et al. Efficacy and safety studies of a recombinant chimeric respiratory syncytial virus FG glycoprotein vaccine in cotton rats. *Journal of virology* 74, 10287-10292 (2000).

22 Prince, G. A. et al. Enhancement of respiratory syncytial virus pulmonary pathology in cotton rats by prior intramuscular inoculation of formalin-inactivated virus. *Journal of virology* 57, 721-728 (1986).

23 Patel, A. et al. In Vivo Delivery of Synthetic Human DNA-Encoded Monoclonal Antibodies Protect against Ebolavirus Infection in a Mouse Model. *Cell reports* 25, 1982-1993.e1984, doi:10.1016/j.celrep.2018.10.062 (2018).

24 Iizuka, K., Machida, T. & Hirafuji, M. Skeletal muscle is an endocrine organ. *Journal of pharmacological sciences* 125, 125-131 (2014).

25 Mir, L. M., Bureau, M. F., Rangara, R., Schwartz, B. & Scherman, D. Long-term, high level in vivo gene expression after electric pulse-mediated gene transfer into skeletal muscle. *Comptes rendus de l'Academie des sciences. Serie III, Sciences de la vie* 321, 893-899 (1998).

26 Maruyama, H. et al. Long-term production of erythropoietin after electroporation-mediated transfer of plasmid DNA into the muscles of normal and uremic rats. *Gene therapy* 8, 461-468, doi:10.1038/sj.gt.3301412 (2001).

27 Rose, E. B., Wheatley, A., Langley, G., Gerber, S. & Haynes, A. Respiratory Syncytial Virus Seasonality—United States, 2014-2017. *MMWR. Morbidity and mortality weekly report* 67, 71-76, doi:10.15585/mmwr.mm6702a4 (2018).

28 Robbie, G. J., Zhao, L., Mondick, J., Losonsky, G. & Roskos, L. K. Population Pharmacokinetics of Palivizumab, a Humanized Anti-Respiratory Syncytial Virus Monoclonal Antibody, in Adults and Children. *Antimicrobial agents and chemotherapy* 56, 4927-4936, doi:10.1128/aac.06446-11 (2012).

29 Griffin, M. P. et al. Safety, Tolerability, and Pharmacokinetics of MEDI8897, the Respiratory Syncytial Virus Prefusion F-Targeting Monoclonal Antibody with an Extended Half-Life, in Healthy Adults. *Antimicrobial agents and chemotherapy* 61, e01714-01716, doi:10.1128/AAC.01714-16 (2017).

30 Unverdorben, F. et al. Pharmacokinetic properties of IgG and various Fc fusion proteins in mice. *mAbs* 8, 120-128, doi:10.1080/19420862.2015.1113360 (2015).

31 Kontermann, R. E. Strategies to extend plasma half-lives of recombinant antibodies. *BioDrugs: clinical immunotherapeutics, biopharmaceuticals and gene therapy* 23, 93-109, doi:10.2165/00063030-200923020-00003 (2009).

32 Wu, H. et al. Development of motavizumab, an ultrapotent antibody for the prevention of respiratory syncytial virus infection in the upper and lower respiratory tract. *Journal of molecular biology* 368, 652-665, doi:10.1016/j.jmb.2007.02.024 (2007).

33 Tiwari, P. M. et al. Engineered mRNA-expressed antibodies prevent respiratory syncytial virus infection. *Nature communications* 9, 3999-3999, doi:10.1038/s41467-018-06508-3 (2018).

34 Pardi, N. et al. Administration of nucleoside-modified mRNA encoding broadly neutralizing antibody protects humanized mice from HIV-1 challenge. *Nat Commun* 8, 14630, doi:10.1038/ncomms14630 (2017).

35 Pardi, N. et al. Expression kinetics of nucleoside-modified mRNA delivered in lipid nanoparticles to mice by various routes. *Journal of controlled release: official journal of the Controlled Release Society* 217, 345-351, doi:10.1016/j.jconrel.2015.08.007 (2015).

36 Thran, M. et al. mRNA mediates passive vaccination against infectious agents, toxins, and tumors. *EMBO molecular medicine*, doi:10.15252/emmm.201707678 (2017).

37 Dismuke, D. J., Tenenbaum, L. & Samulski, R. J. Biosafety of recombinant adeno-associated virus vectors. *Current gene therapy* 13, 434-452 (2013).

Example 2

Herein an engineered single-chain anti-RSV-F variable Fragment (scFv) DMAb is described (Table 1). In vivo delivery of this antibody construct gene resulted in robust systemic levels of the antibody in the serum of mice. Equivalent levels have been associated with protection from lower respiratory disease from RSV infection. In cotton rats, which is the gold-standard to model human disease following RSV infection, maintained serum-expression of the DMAb up to 60 days after delivery is observed. The antibody was also detected in lung-lavage samples, demonstrating effective biodistribution. Furthermore, serum from animals harboring RSV-F scFv DMAb was functionally active in terms of antigen binding and neutralizing live virus. These findings support the significance of dMAb as a viable platform technology to bring monoclonal antibody-based immuno-prophylactics as an economical and effective option to tackle infectious disease.

TABLE 1

| | | | RSV DMAb Plasmids |
| --- | --- | --- | --- |
| DMAb | description | Fc/conformation | Delivery protocol |
| 9206 | Motavizumab | huIgG | 30 min pre-tx Sigma-HYA |
| 9368 | Palivizumab | huIgG | Co-formulation Intropharma HYA |
| 9369 | Palivizumab | huIgG sc-Fv | Co-formulation Intropharma HYA |
| 9370 | Palivizumab | muIgG | Co-formulation Intropharma HYA |
| 9371 | Palivizumab | muIgG sc-Fv | Co-formulation Intropharma HYA |
| 9283 | ADImab | huIgG | Co-formulation hyaluronidase |

Example 3

Here the data presents an engineered anti-RSV-F dMAb and an optimized delivery protocol. Kinetic and magnitude of systemic expression of the dMAb is measured as concentration of the sc-FV IgG dMAb in animal serum. The biodistribution is examined by measuring lung-lavage samples of treated animals. In-vivo expressed dMAbs were also tested for binding and neutralizing functionality.

The data presented herein demonstrates the engineering of anti-RSV sc-Fv encoding DNA plasmid with an improved in-vivo expression profile compared to the full length human IgG. To further enhance systemic expression an optimized delivery protocol was employed. An optimized formulation enhances dispersion of the plasmid DNA through modifications of the extracellular matrix of the target tissue. Electroporation increases cellular uptake of the DNA molecules by target cells. Functionality of in-vivo expressed human sc-Fb\v from serum of treated mice for binding to the RSV-Fusionprotein (RSV-F) antigen and neutralizing live RSV-A virus was confirmed in-vitro. In addition to serum-level expression the in-vivo expressed human sc-Fv was also detected in the lung, the location of natural RSV-infection. Dosing and delivery method was then applied to cotton rats, the standard pre-clinical model for RSV-prophylaxis development.

Figure 12:
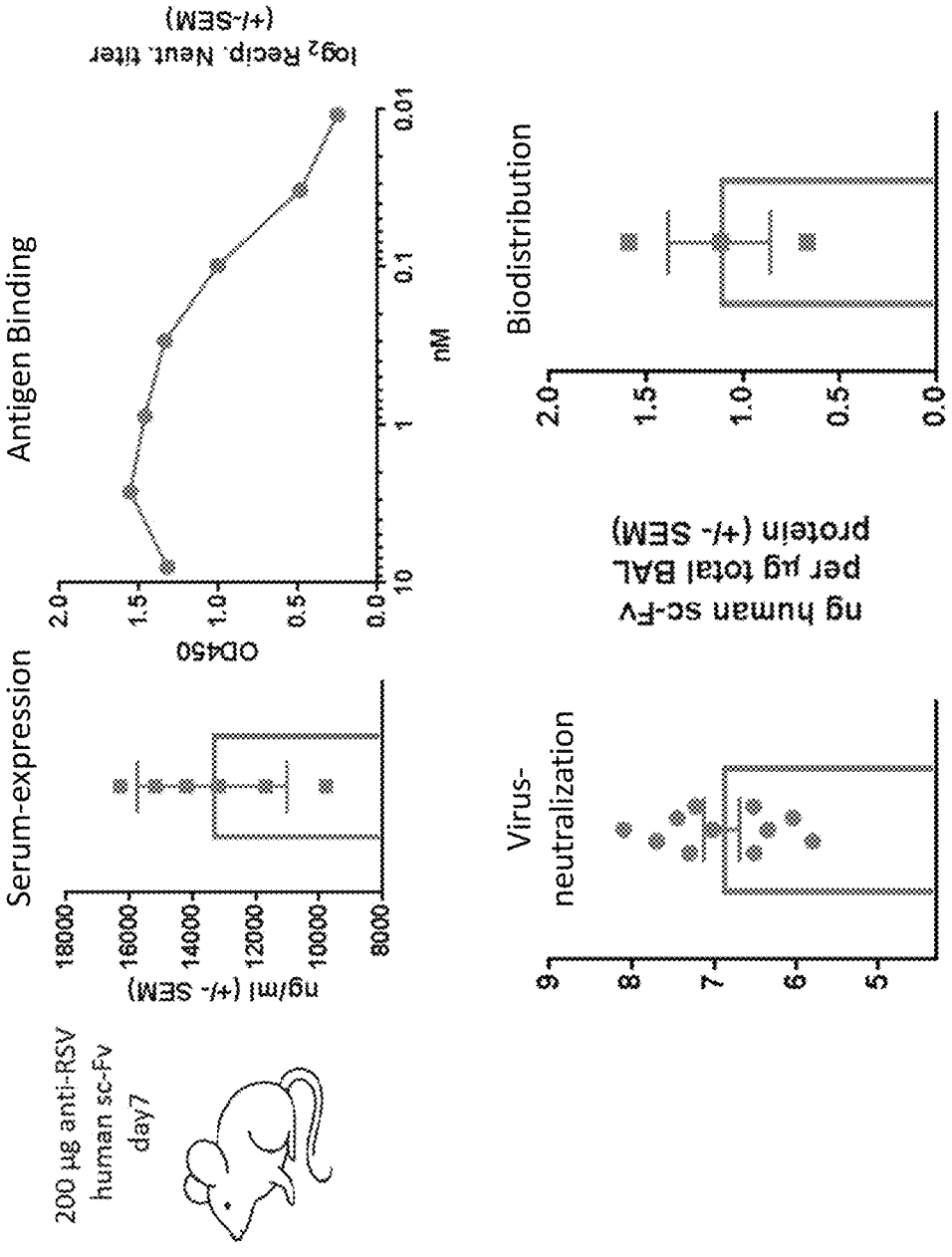
FIG. 12 depicts experimental results demonstrating peak expression and functionality of human sc-Fv anti RSV in immunocompetent mice. Mice were dosed with 200 μg human sc-Fv anti RSV dMAb delivered into leg muscles of balb/c mice. Delivery was assisted by CELLECTRA-3P®. Average serum-level expression of 13200 ng/ml of protein human sc-Fv was achieved 7 days after treatment In-vivo expressed human sc-Fv binds to RSV-F antigen Serum of treated mice exhibits live RSV-A virus-neutralizing activity as demonstrated by the in-vitro plaque reduction assay and results in average of 6.9 log recip. Neut. titer Human sc-Fv is present in the lung of treated mice with an average concentration of 1.1 ng of human sc-Fv per μg of total protein in Bronchioalveolar-lavage (BAL).
Figure 13:
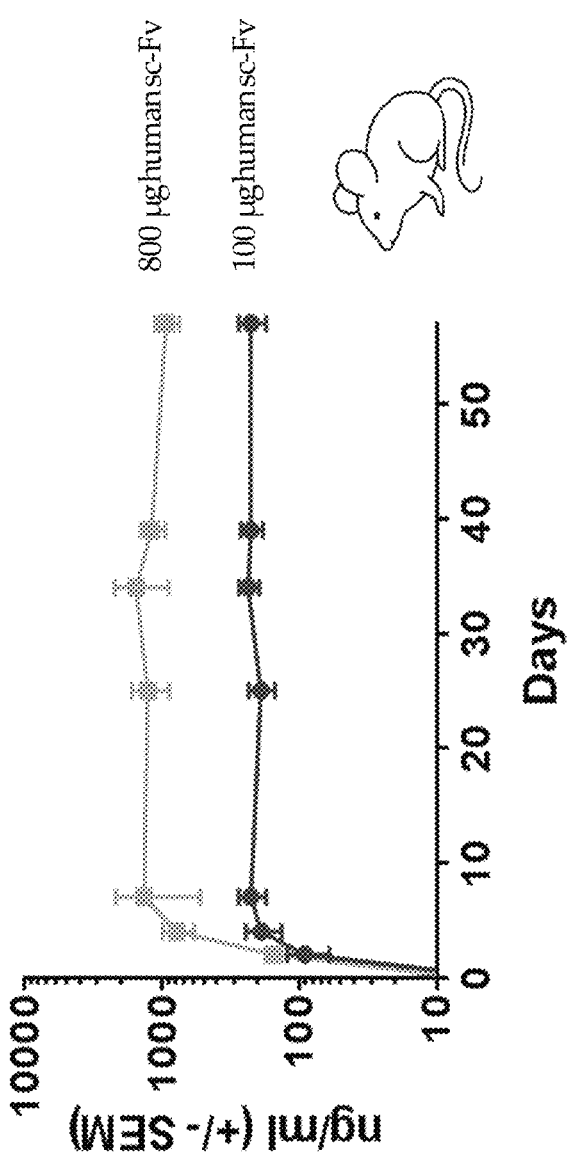
FIG. 13 depicts experimental results demonstrating maintained expression of human sc-Fv in cotton rats. 100 μg and 800 μg of human sc-Fv was delivered into TA muscle of cotton rats. Delivery was assisted with CELLECTRA-3P®. Peak expression in serum is reached after 7 days (226 ng/ml and 1353 ng/ml respectively).
Figure 14:
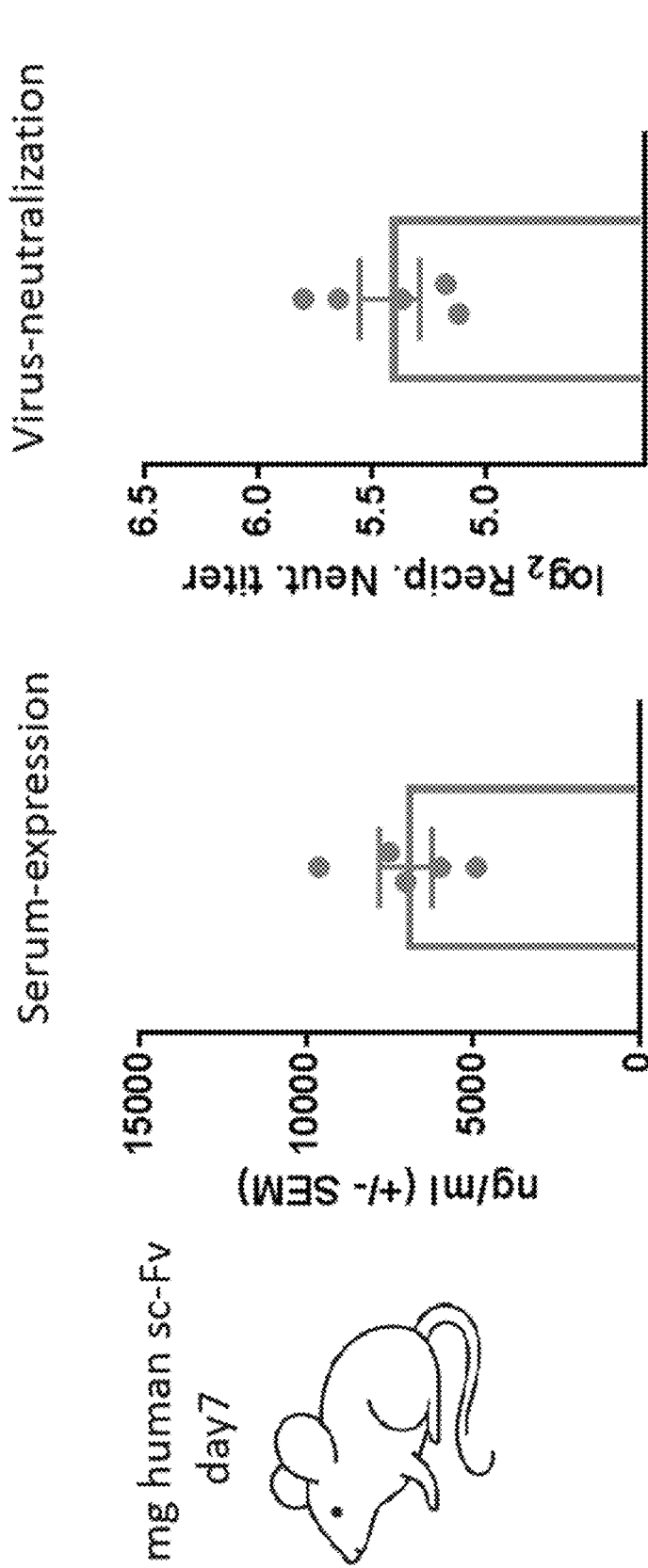
FIG. 14 depicts experimental results demonstrating peak expression and functionality of human sc-Fv in cotton rats. CELLECTRA-3P® assisted delivery of 2.4 mg human sc-Fv in leg muscles of cotton rat results in average serum-expression of 7030 ng/ml at day 7. Serum of treated cotton rats is neutralizing in in-vitro plaque-reduction assay resulting in average of 5.4 log Recip. Neut. Titer.

In vivo delivery of this dMAb resulted in robust systemic levels of the antibody in the serum of mice (FIG. 12). Matched levels of recombinant Pavilizumab provide protection from lower respiratory disease after RSV infection. In cotton rats, which is the gold-standard to model human disease following RSV infection, sustained serum-expression of the dMAb was observed up to 60 days after delivery (FIG. 13). The antibody was also detected in lung-lavage samples, demonstrating effective biodistribution (FIG. 12). Furthermore, serum from animals harboring RSV-F dMAb was functionally active in terms of antigen binding and neutralizing live virus (FIGS. 12 and 14).

These results suggest that the anti-RSV human sc-Fv dMAb could be an effective alternative to repetitive injections of protein-mAb throughout RSV-season. RSV-dMAb has the potential to overcome some of the hurdles associated with the passive immunization.

Example 4

The data presented herein demonstrates the efficacy of RSV dMAbs in a cotton rat model for human RSV-infection. The materials and methods are described.

Intramuscular pDNA Delivery

Mice and cotton rats were shaved over the muscles of their hind legs. RSV-F dMAb plasmid DNA was co-formulated with 128.5 U/ml of hyaluronidase for mice or 117.8 U/ml for cotton rats in 1×SSC.

Figure 15:
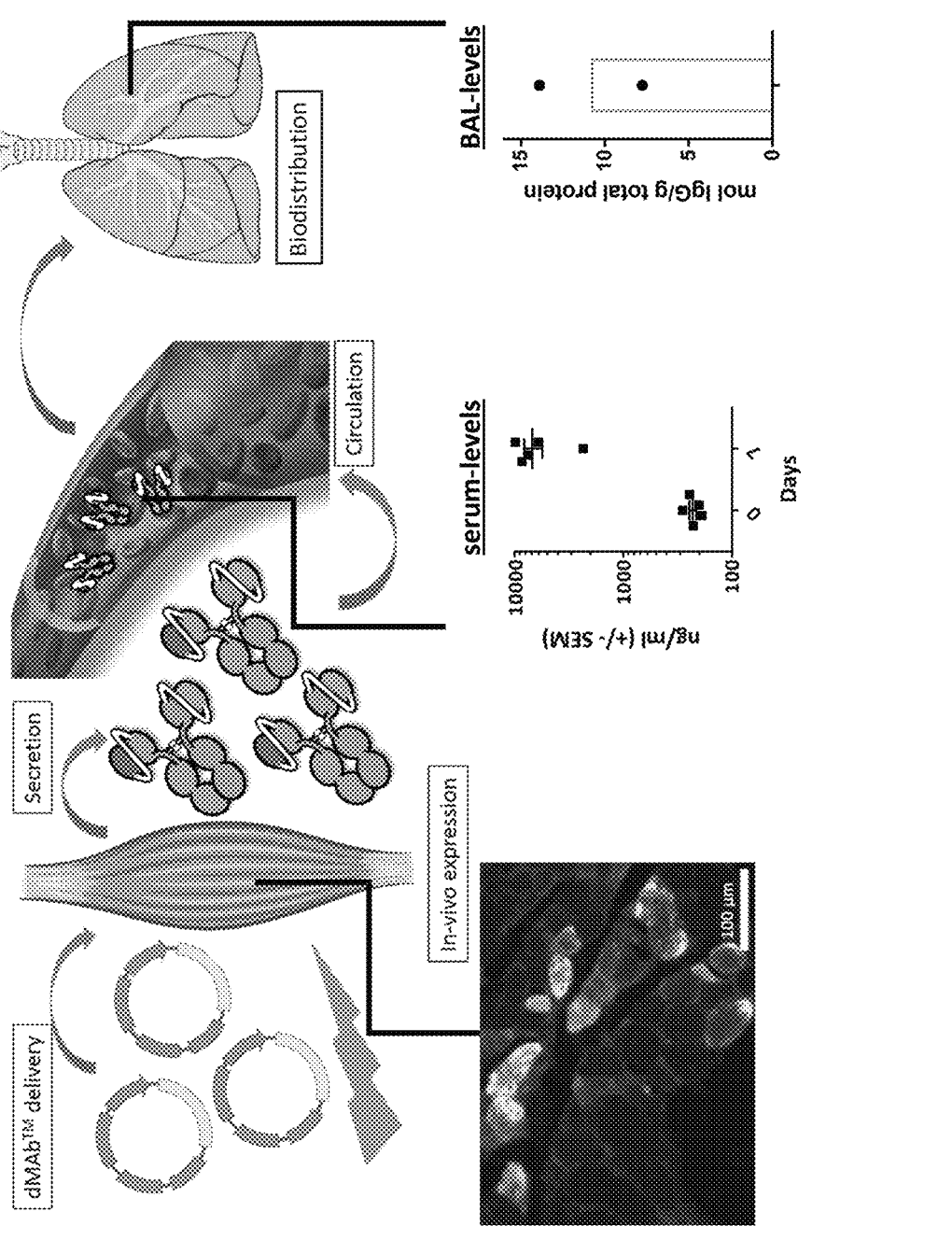
FIG. 15 depicts the RSV-dMAb platform.

Mice received 30 ul and cotton rats 200 ul injections intramuscular (FIG. 15). Injection depth was controlled for 2 mm in mice and 5 mm in cotton rats. 60 seconds after pDNA injection EP was delivered at the injection site with the CELLECTRA-3P®. An array of three needle electrodes with 3 mm insertion depth was used for mice and 6 mm depth for cotton rats.

Quantification of Human Fe RSV-F dMAbs in Animal Serum 96-well assay plates (Thermo Scientific™ Nunc™) were coated with 1 μg/well goat anti-huIgG Fc fragment antibody (Bethyl, TX) in 1×DPBS (Thermofischer, MA) overnight at 4° C. Next day plates were washed with 0.2% (v/v)TWEEN in 1×PBS wash buffer and blocked with 10%(v/v)FBS in 1×DPBS for 1 hourr at room temperature.

The serum samples were diluted in 1% (v/v) FBS in 0.2% (v/v) TWEEN-TxPBS and 100 μl of this mix were added to the assay plate after another washing step. Additionally, a standard dilutions of purified human kappa light chain (Bethyl, TX) were prepared in dilution buffer and added to each assay plate. Samples and standard were incubated for 1 hour at room temperature. After washing, the plates were incubated with a 1:10,000 dilution of goat anti-human IgG kappa light chain HRP (Bethyl, TX) for 1 hour at room temperature. For detection SureBlue Substrate solution (KPL, MD) was added to the washed plates. The reaction was stopped by adding TMB Stop Solution (KPL, MD) after 6 minutes to the assay plates. The O.D. were read at 450 nm. The serum-level expression was interpolated from the standard curve using a sigmoidal four parameter logistic curve fit for log of the concentration.

Cotton Rat Challenge Study

Animals:

Fifteen (15) inbred female *Sigmodon hispidus* cotton rats between 6 and 8 weeks of age (Source: Sigmovir Biosystems, Inc., Rockville MD) were maintained and handled under veterinary supervision. The cotton rats were housed in clear polycarbonate cages individually and provided with standard rodent chow (Harlan #7004) and tap water ad lib.

Challenge Virus:

The prototype Long strain of RSV/A (ATCC, Manassas, VA) was propagated in HEp-2 cells after serial plaque-purification to reduce defective-interfering particles. A pool of virus designated as hRSV/A/Long Lot #021413, prepared in sucrose stabilizing media, and containing approximately $2 \times 10^7$ pfu/ml was used for this in vivo experiment. This stock of virus is stored under −80° C. condition and has been characterized in vivo using the cotton rat model for upper and lower respiratory tract replication.

Procedure:

15 adult female cotton rats (6-8 weeks of age) were divided into three groups of five animals each. Animals of the RSV-dMAb group were treated as described above at day 0 of the experiment. Animals in the Palivizumab control group were injected IM with 0.1 ml of 15 mg/kg Palivizumab on day 6 of the experiment. A third group of animals remained untreated.

At day 7 all animals were challenged with 105 pfu of RSV/A/Long (IN) in a 0.1 mL volume. All animals were sacrificed at day 12. The nose was harvested for viral titration. The lung was harvested en bloc and tri-sected, left section was used for viral titrations and lingular lobe for qPCR.

Lung and Nose Viral Titration

Lung and nose homogenates are clarified by centrifugation and diluted in EMEM. Confluent HEp-2 monolayers are infected in duplicates with diluted homogenates in 24 well plates. After one hour incubation at 37° C. in a 5% $CO_2$ incubator, the wells are overlaid with 0.75% Methylcellulose medium. After 4 days of incubation, the overlay is removed and the cells are fixed with 0.1% crystal violet stain for one hour and then rinsed and air dried. Plaques are counted and virus titer is expressed as plaque forming units per gram of tissue. Viral titers are calculated as geometric mean+standard error for all animals in a group at a given time.

Real-Time PCR

Total RNA is extracted from homogenized lung tissue using the RNeasy purification kit (QIAGEN). One μg of total RNA is used to prepare cDNA using Super Script II RT (Invitrogen) and oligo dT primer (1 μl, Invitrogen). For the real-time PCR reactions the Bio-Rad iQ™ SYBR Green Supermix is used in a final volume of 25 μl, with final primer concentrations of 0.5 μM. Reactions are set up in duplicates in 96-well trays. Amplifications are performed on a Bio-Rad iCycler for 1 cycle of 95° C. for 3 minutes, followed by 40 cycles of 95° C. for 10 seconds, 60° C. for 10 seconds, and 72° C. for 15 seconds. The baseline cycles and cycle threshold (Ct) are calculated by the iQ5 software in the PCR Base Line Subtracted Curve Fit mode. Relative quantitation of DNA is applied to all samples. The standard curves are developed using serially-diluted cDNA sample most enriched in the transcript of interest (e.g., lungs from day 4 post-primary RSV infection). The Ct values are plotted against $\log_{10}$ cDNA dilution factor. These curves are used to convert the Ct values obtained for different samples to relative expression units. These relative expression units are then normalized to the level of b-actin mRNA ("housekeeping gene") expressed in the corresponding sample. For animal studies, mRNA levels are expressed as the geometric mean±SEM for all animals in a group at a given time.

The results are now described.

In-Vivo Expression of RSV-F dMAbs in Cotton Rats

Cotton rats are approximately 4-5 times the size and weight of a mouse. To accommodate these larger rodents, the treatment protocol was modified to larger injection volume of 200 μl and deeper injection depth and penetration of the electroporation electrodes as described in a previous RSV-F cotton rat vaccine study (Smith et al., 2017, Vaccine 35(21):2840-47).

To achieve higher systemic levels of the RSV-dMAb the number of treatment-sites was increased to 6 per animal and a total dose of 2.4 mg dMAb pDNA was able to be delivered. 7 days after the delivery of this optimal dose and day of live virus challenge mean dMAb serum level of 1384.5 ng/ml (SD=189.1, n=4) was measured. RSV-dMAb expression remained stable until the end of the challenge experiment. At day 12 after treatment cotton rat serum contained mean dMAb concentration of 1455.5 ng/ml (SD=345.7, n=4) (FIG. 15).

In comparison mean serum level of human IgG one day after injection of 15 mg/kg Palivizumab was 15290.3 ng/ml (SD=6486.7, n=4) and declined to mean serum-concentration of 10096.6 ng/ml (SD=2110.7, n=5) 5 days after injection.

In-Vivo Expressed RSV-dMAbs Confers Protection from Lower Respiratory Illness

Figure 16:
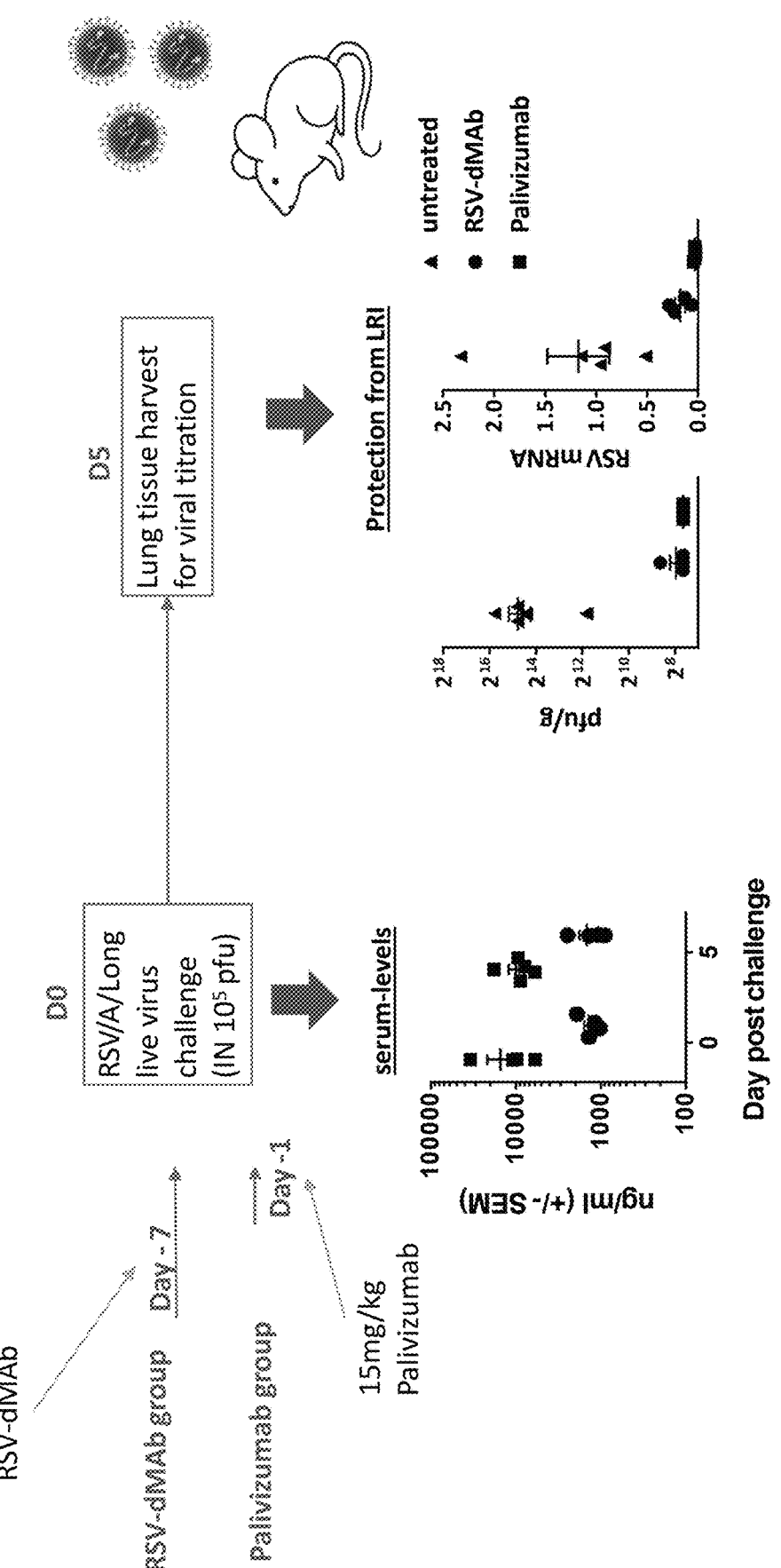
FIG. 16 depicts experimental results demonstrating that RSV dMAb protects cotton rat from LRI following RSV/A challenge.

When challenged with live RSV-A virus, dMAb-treated cotton rats were similarly protected from Lower Respiratory Illness, although RSV-dMAb expression level was almost 10-fold lower than serum-levels after Palivizumab-injection (FIG. 16). The lungs of dMAb-treated cotton rats contained mean viral load of 250 pfu (SEM=50, n=4) 5 days after intranasal challenge. Similar viral load was measured for the lungs of Palivizumab-treated cotton rats: 200 pfu (SEM=0, n=5). In comparison lungs of non-protected cotton rats contained high viral load of 27520 pfu (SEM=8408.9, n=5).

The same trend towards reduced infection of lower respiratory tissue was found when viral genome copy number was measured with real-time PCR using primer targeting the Nonstructural Protein 1 (NS1) of RSV. Mean RSV-mRNA levels in dMAb- (mean RSV mRNA=0.181, SEM=0.050, n=4) and Palivizumab- (mean RSV mRNA=0.032, SEM=0.004, n=5) protected cotton rats were reduced in comparison to non-protected animals (mean RSV mRNA=1.175, SEM=0.306, n=5).

CONCLUSION

The cotton rat is the gold-standard model for human RSV-infection. These animals are susceptible to non-adapted human RSV and display many of the features of the virus-specific human pathology including the symptoms of Vaccine-enhanced Disease (VED) after immunization with the 1960' formalin-inactivated RSV vaccine.

Palivizumab (Synagis) is currently the only FDA-approved preventative option to protect high-risk infants from RSV-associated LRI and hospitalization. As most monoclonal antibody-based therapies, treatment with Palivizumab is expensive and due to temperature-sensitive stability its employment is mostly restricted to settings with highly developed infrastructure.

Protein-Palivizumab and the Palivizumab-based optimized dMAb construct demonstrated similar protection from LRI after RSV-infection in the most relevant pre-clinical model. In general, the manufacturing of dMAb constructs is cost-effective and DNA plasmids are temperature-stable.

DNA-based monoclonal Antibodies in combination with optimized delivery protocols emerge as an advantageous alternative to protein monoclonal Antibodies.

It is understood that the foregoing detailed description and accompanying examples are merely illustrative and are not to be taken as limitations upon the scope of the invention, which is defined solely by the appended claims and their equivalents.

Various changes and modifications to the disclosed embodiments, will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

---

What is claimed is:

1. A composition comprising a nucleic acid molecule encoding a synthetic antibody and hyaluronidase, wherein the nucleic acid molecule comprises a nucleotide sequence encoding ScFv anti-RSV-F synthetic antibody, wherein the nucleic acid molecule comprises nucleotides 742-2220 of SEQ ID NO: 2.

2. The composition of claim 1, wherein the nucleic acid molecule further comprises a nucleotide sequence encoding a cleavage domain.

3. The composition of claim 1, wherein the nucleic acid molecule comprises the nucleotide sequence of SEQ ID NO: 2.

4. The composition of claim 1, wherein the nucleic acid molecule further comprises a nucleotide sequence encoding a leader sequence.

5. The composition of claim 1, wherein the nucleic acid molecule comprises an expression vector.

6. The composition of claim 1, further comprising a pharmaceutically acceptable excipient.

7. A formulation comprising the composition of claim 1.

8. A method of treating Respiratory Syncytial virus infection in a subject, the method comprising administering to the subject the composition of claim 1.

* * * * *

SEQUENCE LISTING

<160> NUMBER OF SEQ ID NOS: 8

<210> SEQ ID NO 1
<211> LENGTH: 5153
<212> TYPE: DNA
<213> ORGANISM: Artificial Sequence
<220> FEATURE:
<223> OTHER INFORMATION: pGX9368

<400> SEQUENCE: 1

```
gctgcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
gtatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttggt     720
accgagctcg gatccgccac catggactgg acatggagaa tcctgttcct ggtggcagca     780
gcaaccggaa cacacgcaca ggtgaccctg agagagtccg gaccagccct ggtgaagcca     840
acccagacac tgaccctgac atgcaccttc tccggctttt ctctgagcac ctccggcatg     900
tctgtgggat ggatcaggca gccccctggc aaggccctgg agtggctggc cgacatctgg     960
tgggacgata agaaggatta caaccctagc ctgaagtccc gcctgacaat cagcaaggac    1020
```

-continued

```
acctccaaga accaggtggt gctgaaggtg acaaatatgg acccagccga tacagccacc      1080
tactattgcg cccggagcat gatcaccaat tggtatttcg acgtgtgggg cgccggaacc      1140
acagtgacag tgagctccgc ctccaccaag ggaccaagcg tgttcccact ggcaccctct      1200
agcaagtcta caagcggcgg caccgccgcc ctgggatgtc tggtgaagga ctacttcccc      1260
gagcctgtga ccgtgtcttg gaacagcggc gccctgacat ccggagtgca cacctttcca      1320
gccgtgctgc agtcctctgg cctgtacagc ctgagctccg tggtgacagt gccctctagc      1380
tccctgggca cacagaccta tatctgcaac gtgaatcaca agccctctaa taccaaggtg      1440
gacaagaagg tggagcctaa gagctgtgat aagacacaca cctgcccacc ctgtccagca      1500
ccagagctgc tgggcggccc tagcgtgttc ctgtttcctc caaagccaaa ggacaccctg      1560
atgatctcca gaacacctga ggtgacctgc gtggtggtgg acgtgtctca cgaggacccc      1620
gaggtgaagt tcaactggta cgtggatggc gtggaggtgc acaatgccaa gaccaagcct      1680
cgggaggagc agtacaacag cacatataga gtggtgtccg tgctgaccgt gctgcaccag      1740
gattggctga acggcaagga gtataagtgc aaggtgtcca ataaggccct gcctgcccca      1800
atcgagaaga caatcagcaa ggccaagggc cagcctaggg agccacaggt gtacaccctg      1860 cccccctagcc gcgacgagct gacaaagaac caggtgtccc tgacctgtct ggtgaagggc      1920
ttctatccat ctgatatcgc cgtggagtgg gagagcaatg gccagcccga gaacaattac      1980
aagaccacac caccgtgct ggactccgat ggctctttct ttctgtattc caagctgacc      2040
gtggacaagt ctaggtggca gcagggcaac gtgttttcct gttctgtgat gcacgaggcc      2100
ctgcacaatc actacacaca gaagagcctg tccctgtctc caggcaagag gggaaggaag      2160
cggagaagcg gctccggagc aaccaacttc tccctgctga agcaggcagg cgatgtggag      2220
gagaatccag gacctatggt gctgcagacc caggtgttta tctctctgct gctgtggatc      2280
agcggcgcct acggcgacat ccagatgaca cagtctccaa gcaccctgtc cgcctctgtg      2340 ggcgatagggg tgacaatcac ctgcaagtgt cagctgagcg tgggctacat gcactggtat      2400
cagcagaagc ccggcaaggc ccctaagctg ctgatctacg acacctctaa gctggcaagc      2460
ggagtgccct cccgcttcag cggctccggc tctggaacag agtttacact gaccatctct      2520
agcctgcagc ccgacgattt cgccacctac tattgctttc agggcagcgg ctatcccttc      2580
accttcggcg gcggcaccaa gctggagatc aagcggacag tggccgcccc cagcgtgttc      2640
atctttcctc catccgacga gcagctgaag tctggcaccg ccagcgtggt gtgcctgctg      2700
aacaatttct accctagaga ggccaaggtg cagtggaagg tggataacgc cctgcagagc      2760
ggcaattccc aggagtctgt gacagagcag gacagcaagg attccaccta ttctctgtcc      2820
tctacactga ccctgtccaa ggccgattac gagaagcaca aggtgtatgc ctgcgaggtg      2880
acacaccagg gcctgagctc ccctgtgacc aagagcttta acagaggcga gtgttgataa      2940
ctcgagtcta gagggcccgt ttaaacccgc tgatcagcct cgactgtgcc ttctagttgc      3000
cagccatctg ttgtttgccc ctcccccgtg ccttccttga ccctggaagg tgccactccc      3060
actgtccttt cctaataaaa tgaggaaatt gcatcgcatt gtctgagtag gtgtcattct      3120
attctggggg gtggggtggg gcaggacagc aaggggggagg attgggaaga caatagcagg      3180
catgctgggg atgcggtggg ctctatggct tctactgggc ggttttatgg acagcaagcg      3240
aaccggaatt gccagctggg cgccctctg gtaaggttgg gaagccctgc aaagtaaact      3300
ggatggcttt cttgccgcca aggatctgat ggcgcagggg atcaagctct gatcaagaga      3360
```

```
caggatgagg atcgtttcgc atgattgaac aagatggatt gcacgcaggt tctccggccg        3420
cttgggtgga gaggctattc ggctatgact gggcacaaca gacaatcggc tgctctgatg        3480
ccgccgtgtt ccggctgtca gcgcaggggc gcccggttct ttttgtcaag accgacctgt        3540
ccggtgccct gaatgaactg caagacgagg cagcgcggct atcgtggctg ccacgacgg         3600 gcgttccttg cgcagctgtg ctcgacgttg tcactgaagc gggaagggac tggctgctat        3660
tgggcgaagt gccggggcag gatctcctgt catctcacct tgctcctgcc gagaaagtat        3720
ccatcatggc tgatgcaatg cggcggctgc atacgcttga tccggctacc tgcccattcg        3780
accaccaagc gaaacatcgc atcgagcgag cacgtactcg gatggaagcc ggtcttgtcg        3840
atcaggatga tctggacgaa gagcatcagg ggctcgcgcc agccgaactg ttcgccaggc        3900
tcaaggcgag catgcccgac ggcgaggatc tcgtcgtgac ccatggcgat gcctgcttgc        3960
cgaatatcat ggtggaaaat ggccgctttt ctggattcat cgactgtggc cggctgggtg        4020
tggcggaccg ctatcaggac atagcgttgg ctacccgtga tattgctgaa gagcttggcg        4080
gcgaatgggc tgaccgcttc ctcgtgcttt acggtatcgc cgctcccgat tcgcagcgca        4140
tcgccttcta tcgccttctt gacgagttct tctgaattat taacgcttac aatttcctga        4200
tgcggtattt tctccttacg catctgtgcg gtatttcaca ccgcatcagg tggcacttt         4260 cggggaaatg tgcgcggaac ccctatttgt ttatttttct aaatacattc aaatatgtat        4320
ccgctcatga caataaacc ctgataaatg cttcaataat agcacgtgct aaaacttcat         4380
ttttaattta aaaggatcta ggtgaagatc cttttttgata atctcatgac caaaatccct       4440
taacgtgagt tttcgttcca ctgagcgtca gaccccgtag aaaagatcaa aggatcttct        4500
tgagatcctt ttttctgcg cgtaatctgc tgcttgcaaa caaaaaaacc accgctacca        4560
gcggtggttt gtttgccgga tcaagagcta ccaactcttt ttccgaaggt aactggcttc        4620
agcagagcgc agataccaaa tactgttctt ctagtgtagc cgtagttagg ccaccacttc        4680
aagaactctg tagcaccgcc tacatacctc gctctgctaa tcctgttacc agtggctgct        4740
gccagtggcg ataagtcgtg tcttaccggg ttggactcaa gacgatagtt accggataag        4800
gcgcagcggt cgggctgaac ggggggttcg tgcacacagc ccagcttgga gcgaacgacc        4860
tacaccgaac tgagatacct acagcgtgag ctatgagaaa gcgccacgct tcccgaaggg        4920
agaaaggcgg acaggtatcc ggtaagcggc agggtcggaa caggagagcg cacgagggag       4980
cttccagggg gaaacgcctg gtatctttat agtcctgtcg ggtttcgcca cctctgactt       5040
gagcgtcgat ttttgtgatg ctcgtcaggg gggcggagcc tatggaaaaa cgccagcaac       5100
gcggcctttt tacggttcct ggccttttgc tggccttttg ctcacatgtt ctt              5153
```

```
<210> SEQ ID NO 2
<211> LENGTH: 4439
<212> TYPE: DNA
<213> ORGANISM: Artificial Sequence
<220> FEATURE:
<223> OTHER INFORMATION: pGX9369

<400> SEQUENCE: 2
```

```
gctgcttcgc gatgtacggg ccagatatac gcgttgacat tgattattga ctagttatta          60
atagtaatca attacggggt cattagttca tagcccatat atggagttcc gcgttacata         120
acttacggta aatggcccgc ctggctgacc gcccaacgac ccccgcccat tgacgtcaat         180
aatgacgtat gttcccatag taacgccaat agggactttc cattgacgtc aatgggtgga         240
gtatttacgg taaactgccc acttggcagt acatcaagtg tatcatatgc caagtacgcc         300
```

-continued

```
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttggt     720
accgagctcg gatccgccac catggtgctg cagacccagg tgtttatttc actgctgctg     780
tggatttcag gagcctacgg ggacattcag atgacccaga gcccttcaac actgtccgcc     840
agcgtgggcg acagagtgac aatcacctgt aagtgccagc tgagcgtggg ctatatgcac     900
tggtatcagc agaagcctgg caaggcccca aagctgctga tctatgacac cagcaagctg     960
gcctctggcg tgccatccag attctccggc tctggcagcg gcaccgagtt tacactgacc    1020
atctccagcc tgcagccaga tgacttcgcc acctactatt gcttccaggg cagcggctat    1080
cccttcacct ttggcggcgg cacaaagctg gagatcaagg gcggcggcgg ctccggcggc    1140
ggcggctctg gcggcggcgg ctctcaggtg accctgagag agtccggccc agccctggtg    1200
aagccaaccc agaccctgac actgacatgc accttctccg gcttcagcct gtccaccagc    1260
ggcatgtccg tgggctggat caggcagccc ccaggcaagg ccctggagtg gctggccgat    1320
atctggtggg acgataagaa ggactacaac ccctccctga gagcagact gaccatcagc    1380 aaggatacca gcaagaacca ggtggtgctg aaggtgacaa atatggaccc agccgatacc    1440
gccacatact actgtgccag atccatgatc acaaattggt acttcgacgt gtggggcgcc    1500
ggcacaaccg tgacagtgag ctctgagcca aagtcctgcg acaagaccca cacctgtcct    1560
ccttgtccag cccccgagct gctgggcggc ccaagcgtgt tcctgtttcc ccctaagcca    1620
aaggataccc tgatgatctc cagaaccca gaggtgacat gcgtggtggt ggacgtgagc    1680
cacgaggacc ccgaggtgaa gttcaattgg tacgtggatg gcgtggaggt gcacaatgcc    1740
aagaccaagc caagagagga gcagtataac tctacatatc gcgtggtgtc cgtgctgaca    1800
gtgctgcacc aggactggct gaatggcaag gagtacaagt gcaaggtgtc caataaggcc    1860
ctgccagccc ctatcgagaa gacaatctcc aaggccaagg ccagcccag agagccacag    1920 gtgtatacac tgccaccctc cagagatgag ctgacaaaga tcaggtgtc cctgacatgt    1980 ctggtgaagg gcttttatcc ctccgatatc gccgtggagt gggagtctaa tggccagccc    2040
gagaataact ataagacaac ccctccagtg ctggactccg atggctcctt tttcctgtat    2100
tccaagctga ccgtggataa gagcaggtgg cagcagggca acgtgttctc ttgttccgtg    2160
atgcacgaag cactgcacaa ccactacacc cagaagtcac tgtcactgtc accaggaaaa    2220
tgataactcg agtctagagg gcccgtttaa acccgctgat cagcctcgac tgtgccttct    2280
agttgccagc catctgttgt ttgcccctcc cccgtgcctt ccttgaccct ggaaggtgcc    2340
actcccactg tcctttccta ataaaatgag gaaattgcat cgcattgtct gagtaggtgt    2400
cattctattc tggggggtgg ggtggggcag gacagcaagg gggaggattg ggaagacaat    2460
agcaggcatg ctggggatgc ggtgggctct atggcttcta ctgggcggtt ttatggacag    2520
caagcgaacc ggaattgcca gctggggcgc cctctggtaa ggttgggaag ccctgcaaag    2580
taaactggat ggctttcttg ccgccaagga tctgatggcg caggggatca agctctgatc    2640
```

-continued

```
aagagacagg atgaggatcg tttcgcatga ttgaacaaga tggattgcac gcaggttctc   2700
cggccgcttg ggtggagagg ctattcggct atgactgggc acaacagaca atcggctgct   2760
ctgatgccgc cgtgttccgg ctgtcagcgc aggggcgccc ggttcttttt gtcaagaccg   2820
acctgtccgg tgccctgaat gaactgcaag acgaggcagc gcggctatcg tggctggcca   2880
cgacgggcgt tccttgcgca gctgtgctcg acgttgtcac tgaagcggga agggactggc   2940
tgctattggg cgaagtgccg gggcaggatc tcctgtcatc tcaccttgct cctgccgaga   3000
aagtatccat catggctgat gcaatgcggc ggctgcatac gcttgatccg gctacctgcc   3060
cattcgacca ccaagcgaaa catcgcatcg agcgagcacg tactcggatg gaagccggtc   3120
ttgtcgatca ggatgatctg gacgaagagc atcaggggct cgcgccagcc gaactgttcg   3180
ccaggctcaa ggcgagcatg cccgacgcg aggatctcgt cgtgacccat ggcgatgcct   3240
gcttgccgaa tatcatggtg gaaaatggcc gcttttctgg attcatcgac tgtggccggc   3300
tgggtgtggc ggaccgctat caggacatag cgttggctac ccgtgatatt gctgaagagc   3360
ttggcggcga atgggctgac cgcttcctcg tgctttacgg tatcgccgct cccgattcgc   3420
agcgcatcgc cttctatcgc cttcttgacg agttcttctg aattattaac gcttacaatt   3480
tcctgatgcg gtattttctc cttacgcatc tgtgcggtat ttcacaccgc atcaggtggc   3540
acttttcggg gaaatgtgcg cggaacccct atttgtttat ttttctaaat acattcaaat   3600
atgtatccgc tcatgagaca ataaccctga taaatgcttc aataatagca cgtgctaaaa   3660
cttcattttt aatttaaaag gatctaggtg aagatccttt ttgataatct catgaccaaa   3720
atcccttaac gtgagttttc gttccactga gcgtcagacc ccgtagaaaa gatcaaagga   3780
tcttcttgag atcctttttt tctgcgcgta atctgctgct tgcaaacaaa aaaaccaccg   3840
ctaccagcgg tggtttgttt gccggatcaa gagctaccaa ctcttttttcc gaaggtaact   3900 ggcttcagca gagcgcagat accaaatact gttcttctag tgtagccgta gttaggccac   3960
cacttcaaga actctgtagc accgcctaca tacctcgctc tgctaatcct gttaccagtg   4020
gctgctgcca gtggcgataa gtcgtgtctt accgggttgg actcaagacg atagttaccg   4080
gataaggcgc agcggtcggg ctgaacgggg ggttcgtgca cacagcccag cttggagcga   4140
acgacctaca ccgaactgag atacctacag cgtgagctat gagaaagcgc cacgcttccc   4200
gaagggagaa aggcggacag gtatccggta agcggcaggg tcggaacagg agagcgcacg   4260
agggagcttc caggggaaa cgcctggtat ctttatagtc ctgtcgggtt cgccacctc   4320 tgacttgagc gtcgattttt gtgatgctcg tcaggggggc ggagcctatg gaaaaacgcc   4380
agcaacgcgg cctttttacg gttcctggcc ttttgctggc cttttgctca catgttctt   4439
```

```
<210> SEQ ID NO 3
<211> LENGTH: 5153
<212> TYPE: DNA
<213> ORGANISM: Artificial Sequence
<220> FEATURE:
<223> OTHER INFORMATION: pGX9370

<400> SEQUENCE: 3
gctgcttcgc gatgtacggg ccagatatac gcgttgacat tgattattga ctagttatta    60
atagtaatca attacggggt cattagttca tagcccatat atggagttcc gcgttacata   120
acttacggta aatggcccgc ctggctgacc gcccaacgac ccccgcccat tgacgtcaat   180
aatgacgtat gttcccatag taacgccaat agggactttc cattgacgtc aatgggtgga   240
gtatttacgg taaactgccc acttggcagt acatcaagtg tatcatatgc caagtacgcc   300
```

-continued

```
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccac catggactgg acctggagaa tcctgttcct ggtggcagca    780
gcaaccggaa cacacgcaca ggtgacactg agggagagcg gacctgccct ggtgaagcca    840
acccagacac tgaccctgac atgcaccttc tctggctttt ccctgtctac cagcggcatg    900
agcgtgggat ggatcaggca gcccctggc aaggccctgg agtggctggc cgacatctgg    960
tgggacgata agaaggatta caaccctct ctgaagagcc gcctgaccat cagcaaggat   1020
acatccaaga accaggtggt gctgaaggtg accaatatgg accctgccga tacagccacc   1080
tactattgtg cccggagcat gatcaccaat tggtactttg acgtgtgggg cgccggcacc   1140
acagtgacag tgagctccgc caagaccaca gccccttccg tgtatcctct ggccccagtg   1200
tgcggcgata ccacaggctc tagcgtgacc ctgggctgtc tggtgaaggg ctacttccca   1260
gagcccgtga cactgacctg gaactccggc tctctgtcct ctggcgtgca cacctttcca   1320
gccgtgctgc agagcgacct gtacacactg agctcctctg tgacagtgac cagctccacc   1380 tggcccaagcc agtccatcac atgcaacgtg gcccaccccg cctctagcac caaggtggat   1440
aagaagatcg agcccagagg ccctacaatc aagccctgtc caccctgcaa gtgtcctgcc   1500
ccaaatctgc tgggcggccc ttccgtgttc atctttcctc caaagatcaa ggacgtgctg   1560
atgatctctc tgagccctat cgtgacctgc gtggtggtgg acgtgtccga ggacgatcca   1620
gatgtgcaga tctcttggtt cgtgaacaat gtggaggtgc acaccgccca gacacagacc   1680
caccgggagg attataacag cacactgaga gtggtgtccg ccctgccaat ccagcaccag   1740
gactggatga gcggcaagga gtttaagtgc aaggtgaaca ataaggatct gcccgcccct   1800
atcgagcgga ccatctccaa gcccaagggc tctgtgagag cccctcaggt gtacgtgctg   1860 cccccctccag aggaggagat gaccaagaag caggtgcacac tgacctgtat ggtgacagac   1920
ttcatgcctg aggatatcta cgtggagtgg accaacaatg gcaagacaga gctgaactat   1980
aagaataccg agccagtgct ggactccgat ggctcttact ttatgtatag caagctgagg   2040
gtggagaaga gaactgggt ggagcgcaat cctattctt gtagcgtggt gcacgagggc   2100
ctgcacaatc accaccacc aaagtccttc tctagaaccc caggcaagag gggaaggaag   2160
cggagaagcg gctccggagc cacaaacttt tccctgctga agcaggcagg cgacgtggag   2220
gagaatccag gacccatggt gctgcagacc caggtgttca tctctctgct gctgtggatc   2280
agcggcgcct acggcgacat ccagatgacc cagtctccca gcacactgtc cgcctctgtg   2340
ggcgatcggg tgacaatcac ctgcaagtgt cagctgtccg tgggctacat gcactggtat   2400
cagcagaagc caggcaaggc ccccaagctg ctgatctatg acacctctaa gctggccagc   2460
ggcgtgcctt ccagattcag cggctccggc tctggcaccg agtttacact gaccatctcc   2520
tctctgcagc cagacgattt cgccacatac tattgctttc agggcagcgg ataccccttc   2580
accttcggcg gcggcacaaa gctggagatc aagagggccg atgccgcccc aaccgtgtcc   2640
```

-continued

```
atcttccctc ccagcagcga gcagctgaca tctggcggcg ccagcgtggt gtgcttcctg      2700
aacaacttct accccaagga catcaacgtg aagtggaaga tcgatggcag cgagcgccag      2760
aacggcgtgc tgaattcctg gaccgaccag gatagcaagg actccacata ctctatgtct      2820
agcacactga ccctgacaaa ggatgagtac gagcggcaca attcctatac ctgcgaggcc      2880
acacacaaga ccagcacatc ccctatcgtg aagtctttta acagaaatga gtgttgataa      2940
ctcgagtcta gagggcccgt ttaaacccgc tgatcagcct cgactgtgcc ttctagttgc      3000
cagccatctg ttgtttgccc ctcccccgtg ccttccttga ccctggaagg tgccactccc      3060
actgtccttt cctaataaaa tgaggaaatt gcatcgcatt gtctgagtag gtgtcattct      3120
attctggggg gtggggtggg gcaggacagc aaggggagg attgggaaga caatagcagg      3180
catgctgggg atgcggtggg ctctatggct tctactgggc ggttttatgg acagcaagcg      3240
aaccggaatt gccagctggg gcgccctctg gtaaggttgg gaagccctgc aaagtaaact      3300
ggatggcttt cttgccgcca aggatctgat ggcgcagggg atcaagctct gatcaagaga      3360
caggatgagg atcgtttcgc atgattgaac aagatggatt gcacgcaggt tctccggccg      3420
cttgggtgga gaggctattc ggctatgact gggcacaaca gacaatcggc tgctctgatg      3480
ccgccgtgtt ccggctgtca gcgcaggggc gcccggttct ttttgtcaag accgacctgt      3540
ccggtgccct gaatgaactg caagacgagg cagcgcggct atcgtggctg gccacgacgg      3600
gcgttccttg cgcagctgtg ctcgacgttg tcactgaagc gggaagggac tggctgctat      3660
tgggcgaagt gccggggcag gatctcctgt catctcacct tgctcctgcc gagaaagtat      3720
ccatcatggc tgatgcaatg cggcggctgc atacgcttga tccggctacc tgcccattcg      3780
accaccaagc gaaacatcgc atcgagcgag cacgtactcg gatggaagcc ggtcttgtcg      3840
atcaggatga tctggacgaa gagcatcagg ggctcgcgcc agccgaactg ttcgccaggc      3900
tcaaggcgag catgcccgac ggcgaggatc tcgtcgtgac ccatggcgat gcctgcttgc      3960
cgaatatcat ggtggaaaat ggccgctttt ctggattcat cgactgtggc cggctgggtg      4020
tggcggaccg ctatcaggac atagcgttgg ctacccgtga tattgctgaa gagcttggcg      4080
gcgaatgggc tgaccgcttc ctcgtgcttt acggtatcgc cgctcccgat tcgcagcgca      4140
tcgccttcta tcgccttctt gacgagttct tctgaattat taacgcttac aatttcctga      4200
tgcggtattt tctccttacg catctgtgcg gtatttcaca ccgcatcagg tggcactttt      4260
cggggaaatg tgcgcggaac ccctatttgt ttatttttct aaatacattc aaatatgtat      4320
ccgctcatga caataaacc ctgataaatg cttcaataat agcacgtgct aaaacttcat      4380
ttttaattta aaaggatcta ggtgaagatc ctttttgata atctcatgac caaaatccct      4440
taacgtgagt tttcgttcca ctgagcgtca gaccccgtag aaaagatcaa aggatcttct      4500
tgagatcctt tttttctgcg cgtaatctgc tgcttgcaaa caaaaaaacc accgctacca      4560
gcggtggttt gtttgccgga tcaagagcta ccaactcttt ttccgaaggt aactggcttc      4620
agcagagcgc agataccaaa tactgttctt ctagtgtagc cgtagttagg ccaccacttc      4680
aagaactctg tagcaccgcc tacatacctc gctctgctaa tcctgttacc agtggctgct      4740
gccagtggcg ataagtcgtg tcttaccggg ttggactcaa gacgatagtt accggataag      4800
gcgcagcggt cgggctgaac ggggggttcg tgcacacagc ccagcttgga gcgaacgacc      4860
tacaccgaac tgagatacct acagcgtgag ctatgagaaa gcgccacgct tcccgaaggg      4920
agaaaggcgg acaggtatcc ggtaagcggc agggtcggaa caggagagcg cacgagggag      4980
cttccagggg gaaacgcctg gtatctttat agtcctgtcg ggtttcgcca cctctgactt      5040
```

-continued

```
gagcgtcgat ttttgtgatg ctcgtcaggg gggcggagcc tatggaaaaa cgccagcaac   5100
gcggcctttt tacggttcct ggccttttgc tggccttttg ctcacatgtt ctt          5153

<210> SEQ ID NO 4
<211> LENGTH: 4442
<212> TYPE: DNA
<213> ORGANISM: Artificial Sequence
<220> FEATURE:
<223> OTHER INFORMATION: pGX9371

<400> SEQUENCE: 4
gctgcttcgc gatgtacggg ccagatatac gcgttgacat tgattattga ctagttatta     60
atagtaatca attacggggt cattagttca tagcccatat atggagttcc gcgttacata    120
acttacggta aatggcccgc ctggctgacc gcccaacgac ccccgcccat tgacgtcaat    180
aatgacgtat gttcccatag taacgccaat agggactttc cattgacgtc aatgggtgga    240
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccac catggtgctg cagactcagg tgtttatttc actgctgctg    780
tggatttccg gcgcttacgg cgacattcag atgacccaga gcccctccac actgagcgcc    840
tccgtgggcg acagagtgac aatcacatgc aagtgtcagc tgtctgtggg ctatatgcac    900
tggtatcagc agaagcccgg caaggcccca aagctgctga tctatgacac ctctaagctg    960
gcctctggcg tgccaagcag attctccggc agcggctccg gcaccgagtt caccctgaca   1020
atctcctctc tgcagccaga cgatttcgcc acatactact gctttcaggg ctccggctac   1080
ccattcacat ttggcggcgg cacaaagctg gagatcaagg cggcggcggc ctccggcggc   1140
ggcggctctg gcggcggcgg ctctcaggtg acactgcggg agtccggccc agccctggtg   1200
aagccaaccc agacactgac actgacctgt acattttccg gcttctctct gtccaccagc   1260
ggcatgagcg tgggctggat cagacagccc cctggcaagg ccctggagtg gctggccgat   1320
atctggtggg acgataagaa ggactacaat ccttccctga gtctagact gaccatctcc   1380 aaggatacct ccaagaatca ggtggtgctg aaggtgacca acatggaccc tgccgataca   1440
gccacctatt actgcgccag aagcatgatc accaactggt actttgacgt gtggggcgcc   1500
ggcacaaccg tgacagtgtc ttccgagcct agaggcccaa ccatcaagcc atgcccaccc   1560
tgtaagtgtc ccgccccaaa cctgctgggc ggcccatccg tgttcatctt tcccccctaag   1620 atcaaggacg tgctgatgat cagcctgagc ccaatcgtga catgcgtggt ggtggacgtg   1680
tccgaggatg acccagatgt gcagatctct tggttcgtga taacgtgga ggtgcacacc   1740 gcccagaccc agaccacag agaggattac aattccacac tgagagtggt gtccgccctg   1800
cctatccagc accaggattg gatgagcggc aaggagttta gtgcaaggt gaacaataag   1860 gacctgcccg ccccaatcga gagaaccatc tccaagccaa agggctctgt gagggcccca   1920
```

-continued

```
caggtgtacg tgctgcctcc tccagaggag gagatgacaa agaagcaggt gacactgacc    1980
tgcatggtga ccgacttcat gcccgaggac atctacgtgg agtggacaaa caatggcaag    2040
acagagctga actataagaa caccgagcca gtgctggatt ccgacggctc ttacttcatg    2100
tactccaagc tgagagtgga gaagaagaac tgggtggagc ggaatagcta ctcctgttcc    2160
gtggtccacg aagggctgca taaccaccac accactaagt cattttcaag aaccccaggc    2220
aaatgataac tcgagtctag agggcccgtt taaacccgct gatcagcctc gactgtgcct    2280
tctagttgcc agccatctgt tgtttgcccc tcccccgtgc cttccttgac cctggaaggt    2340
gccactccca ctgtcctttc ctaataaaat gaggaaattg catcgcattg tctgagtagg    2400
tgtcattcta ttctgggggg tggggtgggg caggacagca aggggagga ttgggaagac     2460 aatagcaggc atgctgggga tgcggtgggc tctatggctt ctactgggcg gttttatgga    2520
cagcaagcga accggaattg ccagctgggg cgccctctgg taaggttggg aagccctgca    2580
aagtaaactg gatggctttc ttgccgccaa ggatctgatg gcgcagggga tcaagctctg    2640
atcaagagac aggatgagga tcgtttcgca tgattgaaca agatggattg cacgcaggtt    2700
ctccggccgc ttgggtggag aggctattcg gctatgactg gcacaacag acaatcggct     2760 gctctgatgc cgccgtgttc cggctgtcag cgcaggggcg cccggttctt tttgtcaaga    2820
ccgacctgtc cggtgccctg aatgaactgc aagacgaggc agcgcggcta tcgtggctgg    2880
ccacgacggg cgttccttgc gcagctgtgc tcgacgttgt cactgaagcg ggaagggact    2940
ggctgctatt gggcgaagtg ccggggcagg atctcctgtc atctcacctt gctcctgccg    3000
agaaagtatc catcatggct gatgcaatgc ggcggctgca tacgcttgat ccggctacct    3060
gcccattcga ccaccaagcg aaacatcgca tcgagcgagc acgtactcgg atggaagccg    3120
gtcttgtcga tcaggatgat ctggacgaag agcatcaggg gctcgcgcca gccgaactgt    3180
tcgccaggct caaggcgagc atgcccgacg gcgaggatct cgtcgtgacc catggcgatg    3240
cctgcttgcc gaatatcatg gtggaaaatg gccgcttttc tggattcatc gactgtggcc    3300
ggctgggtgt ggcggaccgc tatcaggaca tagcgttggc tacccgtgat attgctgaag    3360
agcttggcgg cgaatgggct gaccgcttcc tcgtgcttta cggtatcgcc gctcccgatt    3420
cgcagcgcat cgccttctat cgccttcttg acgagttctt ctgaattatt aacgcttaca    3480
atttcctgat gcggtatttt ctccttacgc atctgtgcgg tatttcacac cgcatcaggt    3540 ggcactttc gggggaaatgt gcgcggaacc cctatttgtt tatttttcta aatacattca     3600
aatatgtatc cgctcatgag acaataaccc tgataaatgc ttcaataata gcacgtgcta    3660
aaacttcatt tttaatttaa aaggatctag gtgaagatcc ttttttgataa tctcatgacc    3720 aaaatccctt aacgtgagtt ttcgttccac tgagcgtcag accccgtaga aaagatcaaa    3780
ggatcttctt gagatccttt ttttctgcgc gtaatctgct gcttgcaaac aaaaaaacca    3840
ccgctaccag cggtggtttg tttgccggat caagagctac caactctttt tccgaaggta    3900
actggcttca gcagagcgca gataccaaat actgttcttc tagtgtagcc gtagttaggc    3960
caccacttca agaactctgt agcaccgcct acatacctcg ctctgctaat cctgttacca    4020
gtggctgctg ccagtggcga taagtcgtgt cttaccgggt tggactcaag acgatagtta    4080
ccggataagg cgcagcggtc gggctgaacg ggggggttcgt gcacacagcc cagcttggag    4140
cgaacgacct acaccgaact gagataccta cagcgtgagc tatgagaaag cgccacgctt    4200
cccgaaggga gaaaggcgga caggtatccg gtaagcggca gggtcggaac aggagagcgc    4260
acgagggagc ttccaggggg aaacgcctgg tatctttata gtcctgtcgg gtttcgccac    4320
```

```
ctctgacttg agcgtcgatt tttgtgatgc tcgtcagggg ggcggagcct atggaaaaac    4380
gccagcaacg cggccttttt acggttcctg gccttttgct ggccttttgc tcacatgttc    4440
tt                                                                    4442

<210> SEQ ID NO 5
<211> LENGTH: 5174
<212> TYPE: DNA
<213> ORGANISM: Artificial Sequence
<220> FEATURE:
<223> OTHER INFORMATION: pGX9383

<400> SEQUENCE: 5
gctgcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
gtatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttggt     720
accgagctcg gatccgccac catggactgg acttggagaa tcctgttcct ggtcgccgcc     780
gcaactggga ctcatgctca ggtgcagctg gtgcagagcg gggcagaggt gaagaagcca     840
ggcagctccg tgaaggtgtc ttgcaaggca agcggcggct ctctgagcac ctacggcatc     900
cactgggtga gcaggcacc aggacagggc ctgagtgggt gggcggcgt gatgaccgtg     960 tacggcaaga ccacatatgg ccagaacttc caggcaggt tgacaatcgc cgtggaccgc    1020
tctaccaata cagcctacat ggagctgtct agcctgacca gcgacgatac cggcacatac    1080
tattgcgcca ccgactctta ctacgtgtgg acaggcagct atcccctcc attcgatctg    1140 tggggccagg gcaccctggt gacagtgtcc tctgcctcta caaagggacc aagcgtgttt    1200
ccactggcac ctagctccaa gtccacctct ggcggcacag ccgccctggg ctgtctggtg    1260
aaggattact ccctgagcc agtgaccgtg tcctggaact ctggcgccct gaccagcgga    1320
gtgcacacat tcccgccgt gctgcagtct agcggcctgt actccctgtc ctctgtggtg    1380
accgtgccta gctcctctct gggcacccag acatatatct gcaacgtgaa tcacaagcct    1440
agcaatacaa aggtggacaa gaaggtggag ccaaagtcct gtgataagac ccacacatgc    1500
cctccctgtc cagcacctga gctgctgggc ggcccaagcg tgttcctgtt ccacccaag    1560 cccaaggaca ccctgatgat ctccagaacc ccagaggtga catgcgtggt ggtggacgtg    1620
tctcacgagg accccgaggt gaagtttaac tggtacgtgg atggcgtgga ggtgcacaat    1680
gccaagacca gcccccggga ggagcagtac aactccacct atagagtggt gtctgtgctg    1740
acagtgctgc accaggactg gctgaacggc aaggagtata agtgcaaggt gagcaataag    1800
gccctgccag cccccatcga gaagaccatc tccaaggcaa agggacagcc aagggagcca    1860
```

```
caggtgtaca cactgcctcc atcccgcgac gagctgacca agaaccaggt gtctctgaca    1920
tgtctggtga agggcttcta tccctctgat atcgccgtgg agtgggagag caatggccag    1980
cctgagaaca attacaagac cacacccct gtgctggaca gcgatggctc cttctttctg     2040
tattccaagc tgaccgtgga caagtctcgg tggcagcagg gcaacgtgtt tagctgctcc    2100
gtgatgcacg aggccctgca caatcactac acccagaagt ctctgagcct gtccccaggc    2160
aagaggggaa gaaagcggag atctggcagc ggcgccacaa acttcagcct gctgaagcag    2220
gccggcgatg tggaggagaa tcctggccca atggtgctgc agacccaggt gtttatcagc    2280
ctgctgctgt ggatctccgg agcatacgga gagatcgtgc tgacccagac accaggaacc    2340
cagtccctgt ctcctggaca gtccgccaca ctgtcttgta gagccagcca ctccgtgggc    2400
aatgactacc tggcctggta tcagcagaag cctggacaga gcccacggct gctgatccac    2460
ggagcataca ggagggactc cggcatccct gatagattca tcggctctgg cagcggcacc    2520
gactttaccc tgacaatcga tagcctggag cctgacgatt gcgccgtgta ctattgtcag    2580
cagtatggct cctggccact gaccttcggc ggcggcacaa aggtggacat caagaggacc    2640
gtggccgccc ctagcgtgtt catctttcca ccctccgatg agcagctgaa gagcggcaca    2700
gcctccgtgg tgtgcctgct gaacaacttc tacccacgcg aggccaaggt gcagtggaag    2760
gtggacaacg ccctgcagtc tggcaatagc caggagtccg tgaccgagca ggactctaag    2820
gatagcacat attccctgag ctccacctg acactgtcca aggccgatta cgagaagcac    2880
aaggtgtatg cctgtgaggt cacccaccag ggactgtctt cacccgtcac aaaatccttc    2940
aataggggag aatgctgata actcgagtct agagggcccg tttaaacccg ctgatcagcc    3000
tcgactgtgc cttctagttg ccagccatct gttgtttgcc cctcccccgt gccttccttg    3060
accctggaag gtgccactcc cactgtcctt tcctaataaa atgaggaaat tgcatcgcat    3120
tgtctgagta ggtgtcattc tattctgggg ggtggggtgg ggcaggacag caaggggggag   3180 gattgggaag acaatagcag gcatgctggg gatgcggtgg gctctatggc ttctactggg    3240
cggttttatg gacagcaagc gaaccggaat tgccagctgg ggcgccctct ggtaaggttg    3300
ggaagccctg caaagtaaac tggatggctt tcttgccgcc aaggatctga tggcgcaggg   3360
gatcaagctc tgatcaagag acaggatgag gatcgtttcg catgattgaa caagatggat    3420
tgcacgcagg ttctccggcc gcttgggtgg agaggctatt cggctatgac tgggcacaac    3480
agacaatcgg ctgctctgat gccgccgtgt ccggctgtc agcgcagggg cgcccggttc    3540
tttttgtcaa gaccgacctg tccggtgccc tgaatgaact gcaagacgag gcagcgcggc    3600
tatcgtggct ggccacgacg ggcgttcctt gcgcagctgt gctcgacgtt gtcactgaag    3660
cgggaaggga ctggctgcta ttgggcgaag tgccggggca ggatctcctg tcatctcacc    3720
ttgctcctgc cgagaaagta tccatcatgg ctgatgcaat gcggcggctg catacgcttg    3780
atccggctac ctgcccattc gaccaccaag cgaaacatcg catcgagcga gcacgtactc    3840
ggatggaagc cggtcttgtc gatcaggatg atctggacga gagcatcag gggctcgcgc     3900 cagccgaact gttcgccagg ctcaaggcga gcatgcccga cggcgaggat ctcgtcgtga    3960
cccatggcga tgcctgcttg ccgaatatca tggtggaaaa tggccgcttt tctggattca    4020
tcgactgtgg ccggctgggt gtggcggacc gctatcagga catagcgttg gctacccgtg    4080
atattgctga gagcttggc ggcgaatggg ctgaccgctt cctcgtgctt tacggtatcg     4140
ccgctcccga ttcgcagcgc atcgccttct atcgccttct tgacgagttc ttctgaatta    4200
ttaacgctta caatttcctg atgcggtatt ttctccttac gcatctgtgc ggtatttcac    4260
```

```
accgcatcag gtggcacttt tcggggaaat gtgcgcggaa cccctatttg tttatttttc   4320
taaatacatt caaatatgta tccgctcatg agacaataac cctgataaat gcttcaataa   4380
tagcacgtgc taaaacttca tttttaattt aaaaggatct aggtgaagat ccttttttgat   4440 aatctcatga ccaaaatccc ttaacgtgag ttttcgttcc actgagcgtc agaccccgta   4500
gaaaagatca aaggatcttc ttgagatcct ttttttctgc gcgtaatctg ctgcttgcaa   4560
acaaaaaaac caccgctacc agcggtggtt tgtttgccgg atcaagagct accaactctt   4620
tttccgaagg taactggctt cagcagagcg cagataccaa atactgttct tctagtgtag   4680
ccgtagttag gccaccactt caagaactct gtagcaccgc ctacatacct cgctctgcta   4740
atcctgttac cagtggctgc tgccagtggc gataagtcgt gtcttaccgg gttggactca   4800
agacgatagt taccggataa ggcgcagcgg tcgggctgaa cggggggttc gtgcacacag   4860
cccagcttgg agcgaacgac ctacaccgaa ctgagatacc tacagcgtga gctatgagaa   4920
agcgccacgc ttcccgaagg agaaaggcg gacaggtatc cggtaagcgg cagggtcgga   4980
acaggagagc gcacgaggga gcttccaggg ggaaacgcct ggtatcttta tagtcctgtc   5040
gggtttcgcc acctctgact tgagcgtcga tttttgtgat gctcgtcagg ggggcggagc   5100
ctatggaaaa acgccagcaa cgcggccttt ttacggttcc tggccttttg ctggcctttt   5160
gctcacatgt tctt                                                     5174
```

<210> SEQ ID NO 6
<211> LENGTH: 1478
<212> TYPE: DNA
<213> ORGANISM: Artificial Sequence
<220> FEATURE:
<223> OTHER INFORMATION: pGX9369 nucleotide coding sequence

<400> SEQUENCE: 6

```
ggtgctgcag acccaggtgt ttatttcact gctgctgtgg atttcaggag cctacgggga     60
cattcagatg acccagagcc cttcaacact gtccgccagc gtgggcgaca gagtgacaat    120
cacctgtaag tgccagctga gcgtgggcta tatgcactgg tatcagcaga agcctggcaa    180
ggccccaaag ctgctgatct atgacaccag caagctggcc tctggcgtgc catccagatt    240
ctccggctct ggcagcggca ccgagtttac actgaccatc tccagcctgc agccagatga    300
cttcgccacc tactattgct ccagggcag cggctatccc ttcacctttg gcggcggcac    360
aaagctggag atcaagggcg gcggcggctc cggcggcggc ggctctggcg gcggcggctc    420
tcaggtgacc ctgagagagt ccggcccagc cctggtgaag ccaacccaga ccctgacact    480
gacatgcacc ttctccggct tcagcctgtc caccagcggc atgtccgtgg gctggatcag    540
gcagccccca ggcaaggccc tggagtggct ggccgatatc tggtgggacg ataagaagga    600
ctacaacccc tccctgaaga gcagactgac catcagcaag gataccagca gaaaccaggt    660
ggtgctgaag gtgacaaata tggacccagc cgataccgcc acatactact gtgccagatc    720
catgatcaca aattggtact cgacgtgtg gggcgccggc acaaccgtga cagtgagctc    780
tgagccaaag tcctgcgaca gacccacac ctgtcctcct tgtccagccc ccgagctgct    840
gggcggccca agcgtgttcc tgtttcccc taagccaaag gataccctga tgatctccag    900 aacccagag gtgacatgcg tggtggtgga cgtgagccac gaggaccccg aggtgaagtt    960
caattggtac gtggatggcg tggaggtgca caatgccaag accaagccaa gagaggagca   1020
gtataactct acatatcgcg tggtgtccgt gctgacagtg ctgcaccagg actggctgaa   1080
```

```
tggcaaggag tacaagtgca aggtgtccaa taaggccctg ccagcccta tcgagaagac     1140 aatctccaag gccaagggcc agcccagaga gccacaggtg tatacactgc caccctccag     1200
agatgagctg acaaagaatc aggtgtccct gacatgtctg gtgaagggct tttatccctc     1260
cgatatcgcc gtggagtggg agtctaatgg ccagcccgag aataactata agacaacccc     1320
tccagtgctg gactccgatg ctcctttttt cctgtattcc aagctgaccg tggataagag     1380
caggtggcag cagggcaacg tgttctcttg ttccgtgatg cacgaagcac tgcacaacca     1440
ctacacccag aagtcactgt cactgtcacc aggaaaat                             1478
```

```
<210> SEQ ID NO 7
<211> LENGTH: 493
<212> TYPE: PRT
<213> ORGANISM: Artificial Sequence
<220> FEATURE:
<223> OTHER INFORMATION: pGX9369 Amino Acid Sequence

<400> SEQUENCE: 7

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Thr Leu Ser
                20                  25                  30

Ala Ser Val Gly Asp Arg Val Thr Ile Thr Cys Lys Cys Gln Leu Ser
            35                  40                  45

Val Gly Tyr Met His Trp Tyr Gln Gln Lys Pro Gly Lys Ala Pro Lys
        50                  55                  60

Leu Leu Ile Tyr Asp Thr Ser Lys Leu Ala Ser Gly Val Pro Ser Arg
65                  70                  75                  80

Phe Ser Gly Ser Gly Ser Gly Thr Glu Phe Thr Leu Thr Ile Ser Ser
                85                  90                  95

Leu Gln Pro Asp Asp Phe Ala Thr Tyr Tyr Cys Phe Gln Gly Ser Gly
            100                 105                 110

Tyr Pro Phe Thr Phe Gly Gly Gly Thr Lys Leu Glu Ile Lys Gly Gly
        115                 120                 125

Gly Gly Ser Gly Gly Gly Gly Ser Gly Gly Gly Gly Ser Gln Val Thr
        130                 135                 140

Leu Arg Glu Ser Gly Pro Ala Leu Val Lys Pro Thr Gln Thr Leu Thr
145                 150                 155                 160

Leu Thr Cys Thr Phe Ser Gly Phe Ser Leu Ser Thr Ser Gly Met Ser
                165                 170                 175

Val Gly Trp Ile Arg Gln Pro Pro Gly Lys Ala Leu Glu Trp Leu Ala
            180                 185                 190

Asp Ile Trp Trp Asp Asp Lys Lys Asp Tyr Asn Pro Ser Leu Lys Ser
            195                 200                 205

Arg Leu Thr Ile Ser Lys Asp Thr Ser Lys Asn Gln Val Val Leu Lys
        210                 215                 220

Val Thr Asn Met Asp Pro Ala Asp Thr Ala Thr Tyr Tyr Cys Ala Arg
225                 230                 235                 240

Ser Met Ile Thr Asn Trp Tyr Phe Asp Val Trp Gly Ala Gly Thr Thr
                245                 250                 255

Val Thr Val Ser Ser Glu Pro Lys Ser Cys Asp Lys Thr His Thr Cys
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
```

-continued

```
      290             295               300

Val Thr Cys Val Val Val Asp Val Ser His Glu Asp Pro Glu Val Lys
305                 310               315                 320

Phe Asn Trp Tyr Val Asp Gly Val Glu Val His Asn Ala Lys Thr Lys
                325               330               335

Pro Arg Glu Glu Gln Tyr Asn Ser Thr Tyr Arg Val Val Ser Val Leu
            340               345               350

Thr Val Leu His Gln Asp Trp Leu Asn Gly Lys Glu Tyr Lys Cys Lys
        355               360               365

Val Ser Asn Lys Ala Leu Pro Ala Pro Ile Glu Lys Thr Ile Ser Lys
    370               375               380

Ala Lys Gly Gln Pro Arg Glu Pro Gln Val Tyr Thr Leu Pro Pro Ser
385               390               395               400

Arg Asp Glu Leu Thr Lys Asn Gln Val Ser Leu Thr Cys Leu Val Lys
            405               410               415

Gly Phe Tyr Pro Ser Asp Ile Ala Val Glu Trp Glu Ser Asn Gly Gln
            420               425               430

Pro Glu Asn Asn Tyr Lys Thr Thr Pro Pro Val Leu Asp Ser Asp Gly
        435               440               445

Ser Phe Phe Leu Tyr Ser Lys Leu Thr Val Asp Lys Ser Arg Trp Gln
    450               455               460

Gln Gly Asn Val Phe Ser Cys Ser Val Met His Glu Ala Leu His Asn
465               470               475               480

His Tyr Thr Gln Lys Ser Leu Ser Leu Ser Pro Gly Lys
                485               490
```

```
<210> SEQ ID NO 8
<211> LENGTH: 4
<212> TYPE: PRT
<213> ORGANISM: Artificial Sequence
<220> FEATURE:
<223> OTHER INFORMATION: chemically sytnesized; synthetic construct

<400> SEQUENCE: 8

Leu Ala Leu Ala
1
```